(12) United States Patent
Bahado-Singh

(10) Patent No.: US 10,745,754 B2
(45) Date of Patent: Aug. 18, 2020

(54) METHOD FOR PREDICTING CONGENITAL HEART DEFECT

(71) Applicant: BIOSCREENING AND DIAGNOSTICS LLC, Detroit, MI (US)

(72) Inventor: Ray O. Bahado-Singh, Grosse Pointe Shores, MI (US)

(73) Assignee: Bioscreening & Diagnostics LLC, Detroit, MI (US)

( * ) Notice: Subject to any disclaimer, the term of this patent is extended or adjusted under 35 U.S.C. 154(b) by 246 days.

(21) Appl. No.: 15/039,589

(22) PCT Filed: Nov. 25, 2014

(86) PCT No.: PCT/US2014/067437
§ 371 (c)(1),
(2) Date: May 26, 2016

(87) PCT Pub. No.: WO2015/081110
PCT Pub. Date: Jun. 4, 2015

(65) Prior Publication Data
US 2017/0166965 A1    Jun. 15, 2017

Related U.S. Application Data

(60) Provisional application No. 61/909,779, filed on Nov. 27, 2013.

(51) Int. Cl.
*C12Q 1/6883* (2018.01)
(52) U.S. Cl.
CPC ...... *C12Q 1/6883* (2013.01); *C12Q 2600/118* (2013.01); *C12Q 2600/154* (2013.01); *C12Q 2600/158* (2013.01)

(58) Field of Classification Search
None
See application file for complete search history.

(56) References Cited

U.S. PATENT DOCUMENTS

| | | |
|---|---|---|
| 2003/0152574 A1 | 8/2003 | Logan et al. |
| 2005/0053937 A1 | 3/2005 | Berlin |
| 2009/0162836 A1 | 6/2009 | Widschwendter |
| 2011/0150775 A1 | 6/2011 | Slonim et al. |
| 2012/0021943 A1 | 1/2012 | Tavares et al. |

FOREIGN PATENT DOCUMENTS

| | | |
|---|---|---|
| CN | 103119179 A | 5/2013 |
| WO | WO2007129113 | 11/2007 |
| WO | WO2010062738 | 6/2010 |

OTHER PUBLICATIONS

Xu M, Wu Xy, Li Yg, et al. Relationship of CpG islands methylation of CITED2 and congenital heart disease [J]. Third Mil Med Univ . 2013;35(3):245-6 (abstract only).*
Chowdhury (PLoS One Jan. 2011 vol. 6 Issue 1 e16506 pp. 1-11).*
Michels (Experimental Gerontology 2010 vol. 45 pp. 297-301).*
Feng (PNAS 2010 vol. 107 No. 19 pp. 8689-8694).*
Zhu (Molecular Medicine Reports 2011 vol. 4 pp. 137-143).*
Adalsteinsson et al (PLoS One. Oct. 2012 . . . 7(10): e0046705).*
The Partial Supplementary European Search Report dated Jun. 27, 2017 for European patent appliation No. 14865271.2, 15 pages.
Ghanim, et al., "Possible Association Between Complex Congenital Heart Defects and 11p15 Hypomethylation in Three Patients With Severe Silver-Russell Syndrome", American Journal of Medical Genetics Part A, vol. 161, No. 3, Feb. 7, 2013.
Nagy, et al., "Epigenetic Regulation of 5-lipoxygenase in Phentypic Plasticity of Valvular Interstitial Cells Associated with Aortic Valve Stenosis", Febs Letters, Elsevier, Amsterdam, NL, vol. 586, No. 9, Mar. 20, 2012, pp. 1325-1329.
Sheng, et al., "LINE-1 Methylation Status and Its Association with Tetraology of Fallot in Infants", BMC Medical Genomics, Biomed Central Ltd., London, UK, vol. 5, No. 1, Jun. 6, 2012, p. 20.
Zhu, et al., "Screening for Differential Methylation Status in Fetal Myocardial Tissue Samples with Ventricular Septal Defects by Promotoer Methylation Microarrays", Molecular Medicine Reports, Nov. 30, 2010.
Illumina Infinium HumanMethylation 450 Bead Chip, Sep. 28, 2012; accessed from the internet Apr. 28, 2015; URL: <http://www.ebi.ac.uk/arrayexpress/files-A-MEXP-2255/A-MEXP-2255.adf.txt> p. 80, p. 542.
PCT Search Report and Written Opinion dated Jun. 1, 2015 for PCT Application No. PCT/US14/67437, 13 pages.
Chowdhury, et al., "Maternal Genome-Wide DNA Methylation Patterns and Congenital Heart Defects", PLOS ONE, vol. 6, No. 1, Jan. 2011, pp. 1-11.

(Continued)

*Primary Examiner* — Amanda Haney
(74) *Attorney, Agent, or Firm* — Lee & Hayes, P.C.

(57) ABSTRACT

Particular aspects of the invention confirm significant differences in methylation of cytosine bases in many loci throughout the genome in cases of congenital heart defect (CHD) compared to normal cases without CHD. Additional aspects provide novel methods for the prediction of congenital heart defects that can be applied to embryos, fetuses, newborns and different stages of postnatal life including childhood and any time in later postnatal life, is disclosed. The method is applicable not only to deoxyribonucleic acid (DNA) found in body fluids such as blood, urine, sputum, amniotic fluid and other tissues of affected individuals in pre- and post-natal life. Statistical techniques for estimating an individual's risk of having CHD by comparing the degree of methylation of specific cytosine loci throughout the DNA in an individual being tested and comparing this to the percentage of cytosine at sites in two populations of individuals: one with CHD and the other a reference population of normal cases without CHD, are described. Individual risk for having specific types of CHD or CHD overall can also be determined based on the invention.

16 Claims, No Drawings

(56) References Cited

OTHER PUBLICATIONS

The Extended European Search Report dated Oct. 19, 2017 for European Patent Application No. 14865271.2, 17 pages.
Illumina Infinium HumanMethylation 450 Bead Chip, Sep. 2012; accessed from the internet Apr. 28, 2015; URL: <http://www.ebi.ac.uk/arrayexpress/files-A-MEXP-2255/A-MEXP-2255.adf.txt> p. 80, p. 542.
Masliah, et al., "Distinctive patterns of DNA methylation associated with Parkinson disease", Epigenetics, vol. 8, No. 10, Oct. 2013, pp. 1030-1038.
The European Office Action dated Aug. 30, 2018 for European Patent Application No. 14865271.2, a counterpart Foreign Application of U.S. Appl. No. 15/039,589, 6 pages.
The European Office Action dated May 15, 2019 for European Patent Application No. 14865271.2, a counterpart of U.S. Appl. No. 15/039,589, 4 pages.
Translated the Chinese Office Action dated Nov. 15, 2019 for Chinese Patent Application No. 201480065039.X, a counterpart of U.S. Appl. No. 15/039,589, 7 pages.

* cited by examiner

METHOD FOR PREDICTING CONGENITAL HEART DEFECT

CROSS REFERENCE TO RELATED APPLICATION

The present application is a U.S. National Phase Application of International Application No. PCT/US2014/67437, filed Nov. 25, 2014, which claims the benefit of U.S. Provisional Application No. 61/909,779, filed Nov. 27, 2013, both of which are hereby incorporated by reference in their entirety.

FIELD OF THE INVENTION

The invention relates to the application of known techniques for the identification and quantification of differences in the chemical structure of the cytosine nucleotide component of the DNA, so-called DNA methylation, in newborns and other individuals with CHD compared to normal ("unaffected", "control") cases i.e. without CHD, for the purpose of determining the risk or likelihood of a tested individual having CHD. Because of the universal presence of DNA in human cells and tissues, and outside of cells but present on body fluids the technique is applicable to any of these sources of DNA prenatal and any time after birth, for the purposes of estimating risk or likelihood of an individual having as noted above, the invention also applies to DNA that has been released from cells that have undergone destruction, so-called cell-free DNA (cfDNA), and which is found in the body fluids of individuals.

The chemical changes described—so called "DNA methylation" involve the addition of an extra carbon atom (—C—) to the cytosine component nucleotide, one of the known building blocks of DNA. Comparison of differences in cytosine nucleotide methylation at multiple loci or sites throughout the DNA is compared between CHD and non-CHD groups or populations. When methylation levels of an individual undergoing testing is compared to corresponding loci in these two population groups the likelihood of CHD can be determined. Any source of DNA can be used for the methylation studies to predict CHD risk at any stage of prenatal or postnatal life provided the appropriate reference populations are used.

BACKGROUND

Birth defects, i.e. abnormalities developing in fetal life and present at birth, is the major cause of infant death, defined as death within a year of birth, in the USA. Congenital heart defects occur with a frequency of 8-9 cases per 1,000 live births. CHD is the most common group of severe birth defects and is the most costly in terms of hospitalization. Up to 25% of cases with major CHD in newborns are not diagnosed prior to discharge from the hospital.

Congenital aortic valve stenosis (AVS), defined as incomplete obstruction of the valve orifice, is an important category of structural heart defect, and occurs in 3-6% of such cases. There is variability in both the site of obstruction and severity of the obstruction. Sites of obstruction are sub-classified as valvular, subvalvular and supravalvular. About half of infants with severe AVS require surgery. Mild aortic stenosis is difficult to detect in prenatal life, however critical aortic stenosis can lead to left ventricular myocardial dysfunction with endocardial fibroelastosis, left atrial dilation and narrowing of the aortic root. These changes can be a prelude to the development of hypoplastic left heart syndrome.

Based on the high percentage of major CHD that fail to be diagnosed in newborns, it has been recommended that measurement and monitoring of tissue oxygen levels "pulse oximetry" be performed in all newborns to detect low tissue oxygen levels which may be a sign of the presence of a major CHD. There is a clear need to develop screening tests and other markers for the accurate prediction of CHD in the general population both in newborns and also in later stages of postnatal life.

Heart development in embryonic and fetal life requires the coordination and orchestration of a large number of different genes. A relatively small percentage of CHD cases is known to be related to gene mutations which are changes in the normal sequence in which the basic building block ("nucleotides") are arranged in the DNA of the gene. Such mutations lead to malfunctioning or nonfunctioning of genes (i.e. altered amounts, of or the production of abnormal types of proteins) that are important for normal heart development.

In the last six decades an important mechanism for controlling gene function called "epigenetics" has been discovered and extensively investigated. Epigenetics is defined as heritable (i.e. passed onto offspring) changes in gene expression that are not due to mutations i.e. changes in the sequence of, loss or gain of nucleotides in the gene. Rather, epigenetics is a reversible regulation of gene expression by several other potential mechanisms. One such mechanism which is currently the most extensively studied is DNA methylation. Other mechanisms include: changes on the 3 dimensional structure of the DNA, histone protein modification or micro-RNA inhibitory activity.

Cytosine methylation is chemically stable and can be measured in DNA from any source including fresh, stored or archived tissues such as DNA preserved in pathology slides or formalin-fixed paraffin blocks. In addition DNA released from destroyed cells and present in body fluids, cfDNA, can also be a tested for cytosine methylation.

The methylation of cytosine nucleotides within a gene, particularly in the promoter region (which controls gene expression) of said gene is known to be a mechanism of controlling overall gene activity. Classically, the methylation of cytosine is associated with inhibition of gene transcription. However, in certain genes, methylation of cytosine is known to have the reverse effect i.e. promotion of gene transcription.

Commonly used techniques for measuring cytosine methylation include but are not limited to bisulfite-based methylation assay. The addition of bisulfite to DNA results in the conversion of unmethylated cytosine results in the methylation of the cytosine (i.e. addition of an extra carbon atom to position #5 of the hexagonal ring structure of the cytosine nucleotide) and its ultimate conversion to the nucleotide uracil. Uracil has similar binding properties to thiamine in the DNA sequence. Previously methylated cytosine does not undergo this chemical conversion on exposure to bisulfate. Bisulfite assays can thus be used to discriminate previously methylated versus unmethylated cytosine.

Thus the methylation status of cytosine throughout the DNA can be said to indicate the relative expression status of multiple genes throughout the genome. The technique therefore permits simultaneous analysis of the relative level of activation of multiple genes directly or indirectly involved in cardiac development since the mechanism of action of external substances and influences on the cell is largely through their effect on gene function, genome wide DNA methylation also represents the integrated effect of a large number of external (prenatal alcohol and tobacco exposure, anti-folate metabolites etc.) and internal influences on the numerous genes involved in cardiac development. Overall therefore, the differences in cytosine methylation in CHD and normal groups can be used to estimate the risk of and predict the likelihood of CHD in an individual by comparing their cytosine methylation levels to appropriate reference standards.

Despite the frequency and importance of CHD, there is no laboratory test for the routine population screening of embryos, fetuses, newborns or in later stages of post-natal life for CHD. There is a significant need for screening tests that will facilitate the early identification of, medical surveillance of, and treatment of newborns and other individuals with CHDs.

SUMMARY OF THE INVENTION

The inventors have shown that statistically highly significant differences exist in the percentage or level of methylation of individual cytosine nucleotides distributed throughout the genome when cases with common CHD are compared to normal unaffected cases. Cytosines demonstrating methylation differences are distributed both inside and outside of CpG islands and genes. The invention provides methylation markers for distinguishing individual categories of CHD and CHD overall from normal cases.

Particular aspects provide a panel of cytosine markers for distinguishing individual categories of common CHD from normal cases and also for distinguishing CHD as a group from normal cases without CHD. The invention relates to risk assessment at any time or period during postnatal life.

Further aspects of the present invention relate to the measurements of cytosine methylation and its use in distinguishing common categories of CHD from each other.

Additional aspects include the use of statistical algorithms and methods for estimating the individual risk of CHD based on methylation levels at informative cytosine loci.

In one embodiment, the invention provides a method for predicting Congenital Heart Defect based on measurement of the frequency or percentage methylation of cytosine nucleotides in various identified loci in the DNA of individuals. In some embodiments, the method comprises the steps of: A) Obtaining a sample from a patient; B) Extracting DNA from blood specimens; C) Assaying to determine the percentage methylation of cytosine at loci throughout the genome; D) Comparing the cytosine methylation level of the patient to a well characterized population of normal and Congenital Heart Defect groups; and E) Calculating the individual risk of Congenital Heart Defect based on the cytosine methylation level at different sites throughout the genome.

In some embodiments, the sample is selected from the group consisting of blood, plasma, serum, urine, sputum and amniotic fluid.

In some embodiments, the methylation sites are used in many different combinations to calculate the probability of Congenital Heart Defect in an individual.

In some embodiments, the patient is an embryo or fetus. In some embodiments, the patient is a newborn. In some embodiments, the patient is a pediatric patient.

In some embodiments, the invention further comprises determining the risk or predisposition to having a Congenital Heart Defect at any time during any period of postnatal life.

In some embodiments, the DNA is obtained from cells. In some embodiments, the DNA is cell free. In some embodiments, the DNA is DNA of a fetus obtained from maternal body fluids or placental tissue. In some embodiments, the DNA is obtained from amniotic fluid, fetal blood or cord blood obtained at birth.

In some embodiments, the sample is obtained and stored for purposes of pathological examination. In some embodiments, the sample is stored as slides, tissue blocks, or frozen.

In other embodiments, the Congenital Heart Defect is aortic valve stenosis (AVS), hypoplastic left heart syndrome (HLHS), ventricular septal defect (VSD), Tetralogy of Fallot (TOF), coarctation of the aorta (Coarct), atrial septal defect (ASD) or pulmonary stenosis (PS).

In some embodiments: the Congenital Heart Defect is VSD and the different sites are two or more of the loci identified in Table 1; the Congenital Heart Defect is ASD and the different sites are two or more of the loci identified in Table 2; the Congenital Heart Defect is PS and the different sites are two or more of the loci identified in Table 3; the Congenital Heart Defect is coarctation of the aorta and the different sites are two or more of the loci identified in Table 4; the Congenital Heart Defect is TOF and the different sites are two or more of the loci identified in Table 5; or the Congenital Heart Defect is HLHS and the different sites are two or more of the loci identified in Table 6.

In some embodiments, measurement of the frequency or percentage methylation of cytosine nucleotides is obtained using gene or whole genome sequencing techniques.

In another embodiment, the assay is a bisulfite-based methylation assay.

In one embodiment, the invention provides a method by which proteins transcribed from the genes described can be measured in body fluids (maternal and affected individuals) and used to detect and distinguish different types of CHD.

In another embodiment mRNA produced by affected genes is measured in tissue or body fluids and mRNA levels can be quantitated to determine activity of said genes and used to estimate likelihood of CHD. In some embodiments, the method further comprises the use of an mRNA genome-wide chip for the measurement of gene activity of genes genome-wide for screening tissue (including placenta) or body fluids (including blood, amniotic fluid and saliva).

In some embodiments, proteins transcribed from related genes can be measured and quantitated in body fluids and or tissues of pregnant mothers or affected individuals.

DETAILED DESCRIPTION OF THE INVENTION

Aspects of the current invention confirm highly significant differences in the percentage methylation of cytosine nucleotides throughout the genome in individuals with common categories of CHD and normal groups using a widely available commercial bisulfite-based assay for distinguishing methylated from unmethylated cytosine. Cytosines analyzed for this invention were not limited to CpG islands or to specific genes but included cytosine loci outside of CpG islands and outside of genes. For the purposes of this particular invention only cytosine loci associated with known genes were reported. Significant differences in cytosine methylation loci throughout the genome were observed not only between specific categories (total of 6) of CHD and a normal study group but between the combined CHD group versus normal group and finally between a two common categories of CHD.

Particular aspects provide panels of known and identifiable cytosine loci throughout the genome whose methylation levels (expressed as percentages) is useful for distinguishing CHD from normal cases.

Additional aspects describe the capability of combining other recognized CHD risk factors including but not limited to family history, mutations of folate metabolizing enzymes and maternal exposure to various toxins such as alcohol and tobacco (during the relevant pregnancy) along with cytosine methylation data for the prediction of CHD. Multiple individual cytosine loci demonstrate highly significant differences in the degree of their methylation in CHD versus normal cases (FDR q-values $1.0 \times 10^{-3}$ to $1.0 \times 10^{-35}$) see below.

In the particular analyses presented, 8 cases of hypoplastic left heart (HLH), 8 cases of ventricular septal defects (VSD), 12 cases each from the categories of pulmonary stenosis (PS), atrial septal defect (ASD) and coarctation of the aorta (Coarct) and 14 cases of tetralogy of fallot (TOF), were each compared as separate groups compared to a combined group of 32 normal control cases. All six individual categories of CHD (total of 64) cases were combined to form a single group and compared to the combined group of 32 normals to determine whether CHD cases as a whole could be distinguished from non-CHD or normal cases. Highly significant differentiation in methylation levels were identified in cytosine loci when each individual CHD category was compared to the normal group (Tables 1-6). CHD cases were compared as a single group to the combined normal group (Table 7). The tables were limited to cytosines located within known genes. We found highly significant differences in cytosine methylation levels. For each category of CHD, highly significant differences in multiple cytosine methylation sites were demonstrated between CHD and normal cases. Combinations of these methylation loci were very sensitive predictors of individual and combined CHDs (Tables 8-19).

Definitions:

Ventricular septal defect (VSD) refers to one or more holes in the dividing wall which separates the two pumping chambers or left and right ventricles of the heart. This results in the mixing of blood with high and low oxygen content from these two chambers.

Teralogy of Fallot is a heart defect in which a number of structural abnormalities of the heart and the vessels arising from the heart are found. These abnormalities include narrowing of the main artery to the lungs (pulmonary artery), ventricular septal defect (see above), overriding aorta (displacement of one of the main vessel from the heart, known as the aorta, thus causing it to sit astride the dividing wall or 'septum' between the left and right ventricles). Finally, thickening or 'hypertrophy' of the muscles of the right ventricle occurs.

Hypoplastic left heart syndrome (HLH) is a condition in which the left side of the heart, more specifically the left ventricle (or left "pumping" chamber of the heart), is severely underdeveloped. As a result the heart is unable to pump blood containing high levels of oxygen to the brain and the rest of the body.

Atrial septal defect is a condition in which there is an abnormal hole in the wall separating the two atria or receiving chambers of the heart. These atria normally receive blood from the lungs as well as the rest of the body and then push the blood into the pumping chambers or ventricles.

Coarctation of the aorta represents a narrowing of the aorta, which is one of the two main vessels of the heart, and which carries oxygenated blood from the left side of the heart to the brain and the rest of the body.

Finally, Pulmonary stenosis is a condition in which there is narrowing of the vessel (pulmonary artery) that carries low oxygen content blood from the right side of the heart to the lungs. The narrowing usually occurs at the level of the pulmonary valve which ensures forward flow of blood in the pulmonary artery. Narrowing of the pulmonary artery restricts the flow of blood from the heart to the lungs for proper oxygenation.

These represent six common and clinically important CHD. They frequently require surgery to prevent severe complications and death.

Cytosine refers to one of a group of four building blocks "nucleotides" from which DNA is constructed. The other nucleotides or building blocks found in DNA are thiamine, adenine, and guanosine. The chemical structure of cytosine is in the form of a six sided hexagon or pyrimidine ring.

The term methylation refers to the enzymatic addition of a "methyl group" or single carbon atom to position #5 of the pyrimidine ring of cytosine which leads to the conversion of cytosine to 5-methyl-cytosine. The methylation of cytosine as described is accomplished by the actions of a family of enzymes named DNA methyltransferases (DNMT's). The 5-methyl-cytosine when formed is prone to mutation or the chemical transformation of the original cytosine to form thymine. Five-methylcytosines account for about 1% of the nucleotide bases overall in the normal genome.

The term hypermethylation refers to increased frequency or percentage methylation at a particular cytosine locus when specimens from an individual or group of interest is compared to a normal or control group.

Cytosine is usually paired with guanosine another nucleotide in a linear sequence along the single DNA strand to form CpG pairs. "CpG" refers to a cytosine-phosphate-guanosine chemical bond in which the phosphate binds the two nucleotides together. In mammals, in approximately 70-80% of these CpG pairs the cytosine is methylated (Chatterjee R, Vinson C. Biochemica et Biophisica Acta 2012; 1819: 763-70). The term "CpG island" refers to regions in the genome with high concentration of CG dinucleotide pairs or CpG sites. "CpG islands" are often found close to genes in mammalian DNA. The length of DNA occupied by the CpG island is usually 300-3000 base pairs. The CG cluster is on the same single strand of DNA. The CpG island is defined by various criteria including that the length of recurrent CG dinucleotide pairs occupying at least 200 bp of DNA and with a CG content of the segment of at least 50% along with the fact that the observed/expected CpG ratio should be greater than 60%. In humans about 70% of the promoter regions of genes have high CG content. The CG dinucleotide pairs may exist elsewhere in the gene or outside of and not know to be associated with a particular gene.

Approximately 40% of the promoter region (region of the gene which controls its transcription or activation) (Fatemi M et al. Footprints of mammalian CpG DNA methyltransferases revealing nucleosome positions at a single molecule level. Nucleic Acids Res 2005; 33:e176) of mammalian genes have associated CpG islands and three quarters of these promoter-regions have high CpG concentrations. Overall in most CpG sites scattered throughout the DNA the cytosine nucleotide is methylated. In contrast in the, CpG sites located in the CpG islands of promoter regions of genes the cytosine is unmethylated suggesting a role of methylation status of cytosine in CpG Islands in gene transcriptional activity.

The methylation of cytosines associated with or located in a gene is classically associated with suppression of gene transcription. In some genes however, increased methylation has the opposite effect and results in activation or increased transcription of a gene. One potential mechanism explaining the latter phenomenon could be through the inhibition of gene suppressor elements thus releasing the gene from inhibition. Epigenetic modification, including DNA methylation, is the mechanism by which for example cells which contain identical DNA are able to activate different genes and result in the differentiation into unique tissues e.g. heart or intestines.

Epigenetics is defined as heritable (i.e. passed onto offspring) changes in gene expression of cells that are not primarily due to mutations or changes in the sequence of nucleotides (adenine, thiamine, guanine, and cytosine) in the genes. Rather, epigenetics is a reversible regulation of gene expression by several potential mechanisms. One such mechanism which is the most extensively studied is DNA methylation. Other mechanisms include changes in the 3 dimensional structure of the DNA, histone protein modification, and micro-RNA inhibitory activity.

The receiver operating characteristics (ROC) curve is a graph plotting sensitivity —defined in this setting as the percentage of CHD cases with a positive test or abnormal cytosine methylation levels at a particular cytosine locus on the Y axis and false positive rate (1-specificity)—i.e. the number of normal non-CHD cases with abnormal cytosine methylation at the same locus—on the X-axis. Specificity is defined as the percentage of normal cases with normal methylation levels at the locus of interest or a negative test. False positive rate refers to the percentage of normal individuals falsely found to have a positive test (i.e. abnormal methylation levels).

The area under the ROC curves (AUC) indicates the accuracy of the test in identifying normal from abnormal cases (Hanley J A, McNeil B J. *Radiology* 1982; 143:29-36).

The AUC is the area under the ROC plot from the curve to the diagonal line from the point of intersection of the X- and Y-axes and with an angle of incline of 45°. The higher the area under receiver operating characteristics (ROC) curve the greater is the accuracy of the test in predicting the condition of interest. An area ROC=1.0 indicates a perfect test, which is positive (abnormal) in all cases with the disorder and negative in all normal cases (without the disorder). Methylation assay refers to an assay, a large number of which are commercially available, for distinguishing methylated versus unmethylated cytosine loci in the DNA.

Methylation Assays

Several quantitative methylation assays are available. These include COBRA™ (Ziong and Laird, Nucleic Acid Res 1997 25; 2532-4) which uses methylation sensitive restriction endonuclease, gel electrophoresis and detection based on labeled hybridization probes. Another available technique is the Methylation Specific PCR (MSP) for amplification of DNA segments of interest. This is performed after sodium 'bisulfite' conversion of cytosine using methylation sensitive probes. MethyLight™, a quantitative methylation assay based uses fluorescence based PCR (Eads et al, Cancer Res 1999; 59:2302-2306). Another method used is the Quantitative Methylation (QM™) assay, which combines PCR amplification with fluorescent probes designed to bind to putative methylation sites. Ms-SNuPE™ is a quantitative technique for determining differences in methylation levels in CpG sites. As with other techniques bisulfite treatment is first performed leading to the conversion of unmethylated cytosine to uracil while methyl cytosine is unaffected. PCR primers specific for bisulfite converted DNA is used to amplify the target sequence of interest. The amplified PCR product is isolated and used to quantitate the methylation status of the CpG site of interest (Gonzalgo and Jones Nuclei Acids Res 1997; 25:252-31). The preferred method of measurement of cytosine methylation is the Illumina method.

Illumina Method

For DNA methylation assay the Illumina Infinium® Human Methylation 450 Beadchip assay was used for genome wide quantitative methylation profiling. Briefly genomic DNA is extracted from cells in this case archived blood spot, for which the original source of the DNA is white blood cells. Using techniques widely known in the trade, the genomic DNA is isolated using commercial kits. Proteins and other contaminants were removed from the DNA using proteinase K. The DNA is removed from the solution using available methods such as organic extraction, salting out or binding the DNA to a solid phase support. Bisulfite Conversion As described in the Infinium® Assay Methylation Protocol Guide, DNA is treated with sodium bisulfite which converts unmethylated cytosine to uracil, while the methylated cytosine remains unchanged. The bisulfite converted DNA is then denatured and neutralized. The denatured DNA is then amplified. The whole genome application process increases the amount of DNA by up to several thousand fold. The next step uses enzymatic means to fragment the DNA. The fragmented DNA is next precipitated using isopropanol and separated by centrifugation. The separated DNA is next suspended in a hybridization buffer. The fragmented DNA is then hybridized to beads that have been covalently limited to 50 mer nucleotide segments at a locus specific to the cytosine nucleotide of interest in the genome. There are a total of over 500,000 bead types specifically designed to anneal to the locus where the particular cytosine is located. The beads are bound to silicon based arrays. There are two bead types designed for each locus, one bead type represents a probe that is designed to match to the methylated locus at which the cytosine nucleotide will remain unchanged. The other bead type corresponds to an initially unmethylated cytosine which after bisulfite treatment is converted to a thiamine nucleotide. Unhybridized (not annealed to the beads) DNA is washed away leaving only DNA segments bound to the appropriate bead and containing the cytosine of interest. The bead bound oligomer, after annealing to the corresponding patient DNA sequence, then undergoes single base extension with fluorescently labeled nucleotide using the 'overhang' beyond the cytosine of interest in the patient DNA sequence as the template for extension.

If the cytosine of interest is unmethylated then it will match perfectly with the unmethylated or "U" bead probe. This enables single base extensions with fluorescent labeled nucleotide probes and generate fluorescent signals for that bead probe that can be read in an automated fashion. If the cytosine is methylated, single base mismatch will occur with the "U" bead probe oligomer. No further nucleotide extension on the bead oligomer occurs however thus preventing incorporation of the fluorescent tagged nucleotides on the bead. This will lead to low fluorescent signal form the bead "U" bead. The reverse will happen on the "M" or methylated bead probe.

Laser is used to stimulate the fluorophore bound to the single-base used for the sequence extension. The level of methylation at each cytosine locus is determined by the intensity of the fluorescence from the methylated compared to the unmethylated bead. Cytosine methylation level is expressed as "β" which is the ratio of the methylated-bead probe signal to total signal intensity at that cytosine locus. These techniques for determine cytosine methylation have been previously described and are widely available for commercial use.

The current invention describes the use of a commercially available methylation technique to cover up to 99% Ref Seq genes involving approximately 16,000 genes and 500,000 cytosine nucleotides down to the single nucleotide level, throughout the genome (Infinium Human Methylation 450 Beach Chip Kit). The frequency of cytosine methylation at single nucleotides in a group of CHD cases compared to controls is used to estimate the risk or probability of CHD. The cytosine nucleotides analyzed using this technique included cytosines within CpG islands and those at further distances outside of the CpG islands i.e. located in "CpG shores" and "CpG shelves" and even more distantly located from the island so called "CpG seas".

Identification of Specific Cytosine Nucleotides

Reliable identification of specific cytosine loci distributed throughout the genome has been detailed (Illunnia) in the document: "CpG Loci Identification. A guide to Illumina's method for unambiguous CpG loci identification and tracking for the GoldenGate® and Infinium™ assays for Methylation". A brief summary follows. Illumina has developed a unique CpG locus identifier that designates cytosine loci based on the actual or contextual sequence of nucleotides in which the cytosine is located. It uses a similar strategy as used by NCBI's re SNP IPS (rs#) and is based on the sequence flanking the cytosine of interest. Thus a unique CpG locus cluster ID number is assigned to each of the cytosine undergoing evaluation. The system is reported to be consistent and will not be affected by changes in public databases and genome assemblies. Flanking sequences of 60 bases 5' and 3' to the CG locus (ie. a total of 122 base sequences) is used to identify the locus. Thus a unique "CpG cluster number" or cg# is assigned to the sequence of 122 bp which contains the CpG of interest. Thus only if the 122 bp in the CpG cluster is identical is there a risk of a locus being assigned the same number and being located in more than one position in the genome. Three separate criteria are utilized to track individual CpG locus based on this unique ID system. Chromosome number, genomic coordinate and genome build. The lesser of the two coordinates "C" or "G" in CpG is used in the unique CG loci identification. The CG locus is also designated in relation to the first 'unambiguous" pair of nucleotides containing either an 'A' (adenine) to 'T' (thiamine). If one of these nucleotides is 5' to the CG then the arrangement is designated TOP and if such a nucleotide is 3' it is designate BOT.

In addition, the forward or reverse DNA strand is indicated as being the location of the cytosine being evaluated. The assumption is made that methylation status of cytosine bases within the specific chromosome region is synchronized (Eckhart F, Lewin J, Cortese R et al: DNA methylation profiling of human chromosome 6, 20 and 22. Nat Gent. 38, 1379-85. 2006).

Description of the Methods

A single neonatal dried blood spot saved on filter paper was retrieved from biobank specimens collected as part of the well-established Michigan newborn screening program for the detection of metabolic disorders and stored by the Michigan Department of Community Health (MDCH) in Lansing, Mich. Blood was originally obtained by heel-stick and placed on filter paper generally an average of 2 days after birth. Samples were stored at room temperature. De-identified residual blood spots after the completion of clinical testing were used. IRB approval was obtained by a standardized process through the MDCH. The specimens used for the current study were collected between 1998 and 2003. Cases with chromosomal abnormalities or other known or suspected genetic syndromes including a condition called DiGeorge syndrome in which a portion of the small arm of chromosome #22 is deleted were excluded. The presence of other cardiac or extracardiac anomalies unrelated to the primary diagnosis or the presence of accompanying major birth defects apart from the CHD of interest were excluded.

A total of 8 cases of HLH, 8 cases of VSD, 12 cases each of ASD, coarctation, pulmonary stenosis and 14 cases of TOF, along with a total of 32 controls were analyzed. Control cases were normal non-CHD and non-anomalous newborns. Individual CHD categories were compared to the normal group and also comparisons of all CHD cases grouped together (CHD group) were compared to the normal group as a whole.

Two common CHD categories, VSD and TOF, were compared to each other.

DNA Extraction from Blood-spot

DNA extraction was performed as described in the EZ1® DNA Investigator Handbook, Sample and Assay Technologies, QIAGEN $4^{th}$ Edition, April 2009. A brief summary of the DNA extraction method is provided. Two 6 mm diameter circles (or four 3 mm diameter circles) were punched out of a dried blood spot stored on filter paper and used for DNA extraction. The circle contains DNA from white blood cells from approximately 5 μL of whole blood. The circles are transferred to a 2 ml sample tube.

A total of 190 μL of diluted buffer G2 (G2 buffer:distilled water in 1:1 ratio) was used to elute DNA from the filter paper. Additional buffer is added until residual sample volume in the tube is 190 μL since filter paper will absorb a certain volume of the buffer. Ten μL of proteinase K is added and the mixture is vortexed for 10 s and quick spun. The mixture is then incubated at 56° C. for 15 minutes at 900 rpm. Further incubation at 95° C. for 5 minutes at 900 rpm is performed to increase the yield of DNA from the filter paper. Quick spin was performed. The sample is then run on EZ1 Advanced (Trace, Tip-Dance) protocol as described. The protocol is designed for isolation of total DNA from the mixture. Elution tubes containing purified DNA in 50 μL of water is now available for further analysis.

Infinium DNA Methylation Assay

Methylation Analysis-Illumina's Infinium Human Methylation 450 Bead Chip system was used for genome-wide methylation analysis. DNA (500 ng) was subjected to bisulfite conversion to deaminate unmethylated cytosines to uracils with the EZ-96 Methylation Kit (Zymo Research) using the standard protocol for Infinium. The DNA is enzymatically fragmented and hybridized to the Illumina BeadChips. BeadChips contain locus-specific oligomers and are in pairs, one specific for the methylated cytosine locus and the other for the unmethylated locus. A single base extension is performed to incorporate a biotin-labeled ddNTP. After fluorescent staining and washing, the BeadChip is scanned and the methylation status of each locus is determined using BeadStudio software (Illumina). Experimental quality was assessed using the Controls Dashboard that has sample-dependent and sample-independent controls target removal, staining, hybridization, extension, bisulfite conversion, specificity, negative control, and non-polymorphic control. The methylation status is the ratio of the methylated probe signal relative to the sum of methylated and unmethylated probes. The resulting ratio indicates whether a locus is unmethylated (0) or fully methylated (1). Differentially methylated sites are determined using the Illumina Custom Model and filtered according to p-value using 0.05 as a cutoff.

Illumina's Infinium HumanMethylation450 BeadChip system, an updated assay method that covers CpG sites (containing cytosine) in the promoter region of more genes, i.e., approximately ~16,880. In addition other cytosine loci throughout the genome and outside of genes, and within or outside of CpG islands are represented in this assay.

Cytosine Methylation for the Prediction of CHD Risk Using ROC Curve

To determine the accuracy of the methylation level of a particular cytosine locus for CHD prediction, different threshold levels of methylation e.g. 10%, ≥20%, ≥30%, ≥40% etc. at the site was used to calculate sensitivity and specificity for CHD prediction. Thus for example using ≥10% methylation at a particular cg locus, cases with methylation levels above this threshold would be considered to have a positive test and those with lower than this threshold are interpreted as a negative methylation test. The percentage of CHD cases with a positive test in this example 10% methylation at this particular cytosine locus would be equal to the sensitivity of the test. The percentage of normal non-CHD cases with cytosine methylation levels of <10% at this locus would be considered the specificity of the test. False positive rate is here defined as the number of normal cases with a (falsely) abnormal test result and sensitivity is defined as the number of CHD cases with (correctly) abnormal test result i.e. the level of methylation 10% at this particular cg location. A series of threshold methylation values are evaluated e.g. ≥$\frac{1}{10}$, ≥$\frac{1}{20}$, ≥$\frac{1}{30}$ etc., and used to generate a series of paired sensitivity and false positive values for each locus. A receiver operating characteristic (ROC) curve which is a plot of data points with sensitivity values on the Y-axis and false positivity rate on the X-axis is generated. This approach can be used to generate ROC curves for each individual cytosine locus that displays significant methylation differences between cases and CHD groups.

Standard statistical testing using p-values to express the probability that the observed difference between cytosine methylation at a given locus between CHD and control DNA specimens were performed.

More stringent testing using False discovery Rate (FDR) was also performed. The FDR gives the probability that positive results were due to chance when multiple hypothesis testing is performed using multiple comparisons.

In one embodiment of the invention, using the previously described Illumina Infinium Assays for whole genome methylation studies, significant differences in the frequency (level or percentage) of methylation of specific cytosine nucleotides associated with particular genes were demonstrated in each CHD (VSD, ASD, HLH, coarctation, PS and TOF) group individually when compared to a normal group, and when all CHD categories were combined into a single group ("CHD group") and compared to the normal group. The differences in cytosine methylation levels are highly significant and of sufficient magnitude to accurately distinguish each of the different CHD groups from the normal group. Thus the invention can be used as a test to screen for CHD cases among a mixed population with CHD and normal cases.

The degree of methylation of cytosines could potentially vary based on individual factors (diet, race, age, gender, medications, toxins, environmental exposures, other concurrent medical disorders and so on). Overall, despite these potential sources of variability, whole genome cytosine methylation studies identified specific sites within (and outside of) certain genes and could distinguish and therefore could serve as a useful screening test for identification of groups of individuals predisposed to or at increased risk for having different categories of CHD compared to normal cases.

A further embodiment of the invention is that since cells, with few exceptions (mature red blood cells and mature platelets), contain nuclei and therefore DNA, the invention can be used to screen for CHD using DNA from any cells with the exception of the two named above. In addition cell free DNA from cells that have been destroyed and which can be retrieved from body fluids can be used for such screening.

Cells and DNA from any biological samples which contains DNA can be used for the purpose of this invention. Samples used for testing can be obtained from living or dead tissue and also archeological specimens containing cells or tissues. Examples of biological specimens that can be used to obtain DNA for CHD screening based on this invention include: body fluids (e.g. blood, saliva, genital secretions, urine), skin, hair, follicles/roots, mucous membranes (cheek aka buccal scrapings or scrapings from the tongue), internal body tissue, or umbilical cord blood obtained at birth.

A further embodiment of this invention is the use of genome-wide differences in cytosine methylation in DNA to screen for and determine risk or likelihood of CHD at any stage of prenatal and postnatal life. These stages include the embryo, fetus, the neonatal period (first 28 days after birth), infancy (up to 1 year of age), childhood (up to 10 years of age, adolescence (11 to 21 years of age), and adulthood (i.e. >21 years of age).

The results presented herein confirm that based on the differences in the level of methylation of the cytosine sites between CHD and normal cases throughout the whole human genome, the predisposition to or risk of having a CHD can be determined.

The explanation for the differences in methylation is that the development of CHD results from or leads to abnormal expression of multiple genes many of which directly or indirectly impact or control cardiac development. Abnormal gene function includes either the suppression of the function of genes whose activities are important to normal heart development or conversely the activation of genes whose functions are normally suppressed to permit normal development of the heart. Further, substances that affect the development of CHD for example alcohol, could independently have an effect on other genes that have no relationship to cardiac development but based on "alcohol effect" develop methylation abnormalities. Thus, genome wide cytosine methylation study provides information on the orchestrated widespread activation and suppression of multiple genes and gene networks involved in the normal and abnormal development of the heart. The approach does not require prior knowledge of the role of particular genes in heart development or the mechanism by which changes in the function of the genes lead to CHD. Further, hundreds of thousands of cytosine loci involving thousands of genes are evaluated simultaneously and in an unbiased fashion and can thus be used to accurately estimate the risk of CHD. Of further importance is the fact that cytosine loci outside of the genes can also control gene function, so methylation levels of loci situated outside of the gene further contribute to the prediction of CHD.

The present invention confirms that aberration or change in the methylation pattern of cytosine nucleotide occurs at multiple cytosine loci throughout the genome in individuals affected with different forms of CHD compared to individuals with normal heart development.

Additional aspects of the invention provide techniques and methods for predicting or estimating the risk of CHD based on the differences in cytosine methylation at various DNA locations throughout the genome.

Currently no reliable clinically available biological method using cells, tissue or body fluids exist for predicting or estimating the risk of CHD in individuals in the population.

Several common categories of CHD were examined including aortic valve stenosis (AVS), hypoplastic left heart syndrome (HLHS), ventricular septal defect (VSD), Tetralogy of Fallot (TOF), coarctation of the aorta (Coarct.), atrial septal defect (ASD) and pulmonary stenosis. CHD categories were compared to normal groups and cytosine nucleotides displaying statistically significant differences in methylation status throughout the genome were identified. Because of the extended coverage of cytosine nucleotides, some differentially methylated cytosines were located outside of CpG islands and outside of known genes.

The invention reports a strong association between cytosine methylation status at a large number of cytosine sites throughout the genome using stringent False Discover Rate (FDR) analysis with q-values<0.05 and with many q-values as low as $<1\times10^{-30}$, depending on particular cytosine locus being considered (Tables 1-7). A total of 64 cases of CHD and 32 normal controls were evaluated. Significant differences in cytosine methylation patterns at multiple loci throughout the DNA that was found in all six categories of CHD tested compared to normals and in CHD cases as an overall group compared to normals. The particular cytosines disclosed are located in known genes. The findings are consistent with altered expression of multiple genes in CHD cases compared to controls.

The cytosine methylation markers reported enables population screening studies for the prediction and detection of CHD based on cytosine methylation throughout the genome. They also permit improved understanding of the mechanism of development of CHD for example by evaluating the cytosine methylation data using gene ontology analysis.

The cytosine evaluated in the present application includes but are not limited to cytosines in CpG islands located in the promoter regions of the genes. Other areas targeted and measured include the so called CpG island 'shores' located up to 2000 base pairs distant from CpG islands and 'shelves' which is the designation for DNA regions flanking shores. Even more distant areas from the CpG islands so called "seas" were analyzed for cytosine methylation differences. Thus comprehensive and genome-wide analysis of cytosine methylation is performed.

Statistical Analyses

An aspect of the invention is description of a method for estimating the individual risk of having a particular type of CHD. This calculation can be based on logistic regression analysis leading to identification of the significant independent predictors among a number of possible predictors (e.g. methylation loci) known to be associated with increased risk of CHD. Cytosine methylation levels at different loci can be used by themselves or in combination with other known risk predictors such as for example prenatal exposure to toxins— "yes" or "no" (e.g. alcohol or maternal smoking, maternal diabetes, family history and methylation levels in a single or multiple loci) which are known to be associated with increased risk of the particular type of CHD as described in this application. The probability of an affected individual can be derived from the probability equation based on the logistic regression:

$$P_{CHD}=1/1+e-(B1x_1+B2x_2+B3x_3\ldots Bnx_n)$$

where 'x' refers to the magnitude or quantity of the particular predictor (e.g. methylation level at a particular locus) and "β" or β-coefficient refers to the magnitude of change in the probability of the outcome (a particular type of CHD) for each unit change in the level of the particular predictor (x), the B values are derived from the results of the logistic regression analysis. These B values would be derived from multivariable logistic regression analysis in a large population of affected and unaffected individuals. Values for $x_1, x_2, x_3$ etc, representing in this instance methylation percentage at different cytosine locus would be derived from the individual being tested while the β-values would be derived from the logistic regression analysis of the large reference population of affected (CHD) and unaffected cases mentioned above. Based on these values, an individual's probability of having a type of CHD can be quantitatively estimated. Probability thresholds are used to define individuals at high risk (e.g. a probability of $\geq 1/100$ of CHD may be used to define a high risk individual triggering further evaluation such as an one or more of the following: echocardiograms, pulse oximetry measurements at birth etc, while individuals with risk $<1/100$ would require no further follow-up. The threshold used will among other factors be based on the diagnostic sensitivity (number of CHD cases correctly identified), specificity (number of non-CHD cases correctly identified as normal), risk and cost of ECHOcardiogram and related interventions pursuant to the designation of an individual as "high risk" for CHD and such factors. Logistic regression analysis is well known as a method in disease screening for estimating an individual's risk for having a disorder. (Royston P, Thompson S G. Model-based screening by risk with application in Down's syndrome. *Stat Med* 1992; 11:257-68.)

Individual risk of CHD can also be calculated by using methylation percentages (reported as β-coefficients) at the individual discriminating cytosine locus by themselves or using different combinations of loci based on the method of overlapping Gaussian distribution or multivariate Gaussian distribution (Wald N J, Cuckle H S, Deusem J W et al (1988) Maternal serum screening for down syndrome in early pregnancy. *BMJ* 297, 883-887.) where the variable would be methylation level/percentage methylation at a particular (or multiple) loci so called. Alternatively if methylation percentages or β-coefficients are not normally distributed (i.e. non-Gaussian), normal Gaussian distribution would be achieved if necessary by logarithmic transformation of these percentages.

As an example, two Gaussian distribution curves are derived for methylation at particular loci in the CHD and the normal populations. Mean, standard deviation and the degree of overlap between the two curves are then calculated. The ratio of the heights of the distribution curves at a given level of methylation will give the likelihood ratio or factor by which the risk of having CHD is increased (or decreased) at a particular level of methylation at a given locus. The likelihood ratio (LR) value can be multiplied by the background risk of CHD (for a particular type of CHD, or for CHD overall) in the general population and thus give an individual's risk of CHD based on methylation level at the cg site(s) chosen. Information on the background population risk of CHD in the newborn population is available from several sources (one such example is Hoffman J L et al *Am Heart J* 2004; 147:425-439). Similar information is available for prenatal and later postnatal life.

Evolutionary Computing

Evolutionary computation has been around since the 1950's. These computational methods are tools for predicting outcomes from a complex, large volume of data. Evolutionary computation include a number of approaches such as genetic algorithms. The latter is widely utilized for problem solving and uses the three principles of natural evolution: selection, mutation and recombination [Penza-Reyes C A, Sipper M. Evolutionary computation in medicine 2000; 19:1-23. *Artif Intell Med* 2000; 19:1-23; Whitley D. An overview of evolutionary algorithms: practical issues and common pitfalls. *Info Software Tech* 2001; 43:87-31]. Applications extend from chemistry, economics, engineering, pharmaceuticals to metabolomics. Goodcare [Goodcare R. Making sense of the metabolome using evolutionary computing: seeing the wood with the trees. *J Exp Bot* 2005; 56:245-54.] outlined the acute challenge of analyzing the vast volumes of data generated from new analytic platforms such as metabolomics. He used as an example the analysis of 250 biochemical markers (a very plausible number of data points per patient in epigenetic analysis) to discriminate plants resistant to drought from normal control plants. A complete search to determine whether or not a particular metabolite would be included in the model would require $2^{250}$ or $1.8 \times 10^{75}$ computations. An ultrafast computer would require more than an estimated $3 \times 10^{62}$ years to perform the required computations. Evolutionary computation is an automated method for providing a good solution or predicting the outcome of interest from a large mass of data in a much shorter time.

Evolutionary computation selects 'chromosomes' (which is a 'string' or a combination of different metabolites and their concentrations) that are optimally suited to 'survive' meaning predict the outcome of interest. Each predictor variable (e.g. metabolite) represents a 'gene' on this 'chromosome' string. The 'fitness' to survive of each chromosome is a numerical value from 0 to 1, assigned by the computer program. Fitness indicates how well this combination of parameters ensures 'evolutionary survival' or otherwise stated provides the best answer to the problem [Goodcare R. Making sense of the metabolome using evolutionary computing: seeing the wood with the trees. *J Exp Bot* 2005; 56:245-54].

The combination of the 'chromosome' and the 'fitness' represents an 'individual' [Miranda V, Srinivasan D, Proenca L M. Evolutionary computation in power systems. *Elec Power Energ Sys* 1998; 20:89-981. A population of such 'individuals' represents the 'first generation' of the organisms. The 'individuals' are ranked according to their fitness. This begins the evolutionary process. The selection operator creates the next generation by choosing the fittest individuals from the first generation which have the best chance of 'survival' i.e. predicting the outcome of interest. In addition new 'individuals' for the second generation are created by crossover with random rearrangement of segments of the 'chromosome' i.e. a change in a 'chromosome' segment with its string of constituent predictors (metabolite biomarkers) which form the sequence of 'genes'. Finally, 'mutation' is produced where changes in an individual is introduced. The mutation could mean either changes in constituent predictors or input variables (metabolite markers) with or without any change in their numerical values (concentrations).

Thus genetic algorithms take high performing 'individuals' and selects, 'mutates' and 'recombines' them with other high fitness or high performing 'individuals' to eventually achieve the optimal combination of 'genes' or input predictors on the 'chromosome' that will predict the outcome of interest. The similarities to the well-recognized principles of evolution are obvious. Evolutionary computing including genetic algorithms produces progressively better solutions to the problem through continuous reevaluation and adjustment [Penza-Reyes C A, Sipper M. Evolutionary computation in medicine 2000; 19:1-23. *Artif Intell Med* 2000; 19:1-23.]. The process identifies key components and patterns form a large data set to achieve the highest predictive accuracy. The process is rapid, automated and does not required any statistical or other assumptions about the input variables or outcomes of interest. It is unaffected by missing data, impervious to background noise and does not require parametric distribution. Overall it is said to be superior to regression analyses and neural networks and equally handles both small and extremely large data sets. Given the large number of methylation sites analyzed, approximately 450,000/patient DNA sample and the relatively small number of cases in each CHD category, Genetic Programming a branch of evolutionary computing was the primary method of data analysis. The Gmax computer program version 11.09.23 was used for evolutionary computing analysis.

The use of logistic regression analysis for calculation of sensitivity and specificity for cytosine loci was limited to the overall CHD group (6 categories of CHD combined) as there was insufficient numbers of cases and therefore power in individual CHD subcategories to perform regression analyses.

EXAMPLES

Example 1

Blood spots were collected on filter paper from newborns undergoing routine screening for metabolic disorders. Newborns averaged 2 days of age at the time of collection. Completely de-identified (to researchers) residual blood spots not used for metabolic testing was stored at room temperature at the Michigan Department of Community Health facilities in Lansing, Mich. DNA was extracted and purified from a single spot of blood on filter paper as described previously in the application and methylation levels in different CPG islands determined using the Illumina's Infinium Human Methylation450 Bead Chip system as described earlier.

The level or percentage methylation at multiple cytosine throughout the DNA was compared in 8 cases of VSD type CHD versus 32 normal cases. Table 1 shows 6 cytosine loci located in known genes that were associated with significant differences in methylation between VSD cases and the normal cases. The GENE ID number(s) and GENE symbols, chromosome number on which the gene is located, position of the cytosine locus displaying differential methylation and DNA strand (reverse or forward) are provided along with the contribution (marginal contribution) of each particular cytosine locus for the overall prediction of VSD versus normal non-cardiac cases. The extremely low False discovery Rate (FDR) values indicate the highly significant differences in the percentage methylation between these specific cytosines in VSD cases versus controls.

Example 2

Blood spots were collected on filter paper from newborns undergoing routine screening for metabolic disorders. Newborns averaged 2 days of age at the time of collection. Completely de-identified (to researchers) residual blood spots not used for metabolic testing was stored at room temperature at the Michigan Department of Community Health facilities in Lansing, Mich. DNA was extracted and purified from a single spot of blood on filter paper as described previously in the application and methylation levels in different CPG islands determined using the Illumina's Infinium Human Methylation450 Bead Chip system as described earlier.

The level or percentage methylation at multiple cytosine loci throughout the DNA was compared in 12 cases of ASD type CHD versus 32 normal cases. Table 2 shows 7 cytosine loci located in known genes that were associated with significant differences in methylation between ASD cases and the normal cases. The GENE ID number(s) and GENE symbols are provided along with the contribution (marginal contribution) of each particular cytosine locus for the overall prediction of ASD versus normal non-cardiac cases. The extremely low FDR values indicate the highly significant differences in the percentage methylation between these specific cytosines in VSD cases versus controls.

Example 3

Blood spots were collected on filter paper from newborns undergoing routine screening for metabolic disorders. Newborns averaged 2 days of age at the time of collection. Completely de-identified (to researchers) residual blood spots not used for metabolic testing was stored at room temperature at the Michigan Department of Community Health facilities in Lansing, Mich. DNA was extracted and purified from a single spot of blood on filter paper as described previously in the application and methylation levels in different CPG islands determined using the Illumina's Infinium Human Methylation450 Bead Chip system as described earlier.

The level or percentage methylation at multiple cytosine throughout the DNA was compared in 12 cases of pulmonary stenosis (PS) type CHD versus 32 normal cases. Table 3 shows 6 cytosine loci located in known genes that were associated with significant differences in methylation between PS cases and the normal cases. The GENE ID number(s) and GENE symbols are provided along with the contribution (marginal contribution) of each particular cytosine locus for the overall prediction of PS versus normal non-cardiac cases. The extremely low FDR values indicate the highly significant differences in the percentage methylation between these specific cytosines in PS cases versus controls.

Example 4

Blood spots were collected on filter paper from newborns undergoing routine screening for metabolic disorders. Newborns averaged 2 days of age at the time of collection. Completely de-identified (to researchers) residual blood spots not used for metabolic testing was stored at room temperature at the Michigan Department of Community Health facilities in Lansing, Mich. DNA was extracted and purified from a single spot of blood on filter paper as described previously in the application and methylation levels in different CPG islands determined using the Illumina's Infinium Human Methylation450 Bead Chip system as described earlier.

The level or percentage methylation at multiple cytosine throughout the DNA was compared in 12 cases of coarctation of the aorta ("coarct.") type CHD versus 32 normal cases. Table 4 shows 7 cytosine loci located in known genes that were associated with significant differences in methylation between coarctation cases and the normal cases. The GENE ID number(s) and GENE symbols are provided along with the contribution (marginal contribution) of each particular cytosine locus for the overall prediction of coarctation versus normal non-cardiac cases. The extremely low FDR values indicate the highly significant differences in the percentage methylation between these specific cytosines in coarctation cases versus controls.

Example 5

Blood spots were collected on filter paper from newborns undergoing routine screening for metabolic disorders. Newborns averaged 2 days of age at the time of collection. Completely de-identified (to researchers) residual blood spots not used for metabolic testing was stored at room temperature at the Michigan Department of Community Health facilities in Lansing, Mich. DNA was extracted and purified from a single spot of blood on filter paper as described previously in the application and methylation levels in different CPG islands determined using the Illumina's Infinium Human Methylation450 Bead Chip system as described earlier.

The level or percentage methylation at multiple cytosine throughout the DNA was compared in 14 cases of Tetralogy of Fallot (TOF) type CHD versus 32 normal cases. Table 5 shows 8 cytosine loci located in known genes that were associated with significant differences in methylation between TOF cases and the normal cases. The GENE ID number(s) and GENE symbols are provided along with the contribution (marginal contribution) of each particular cytosine locus for the overall prediction of TOF versus normal non-cardiac cases. The extremely low FDR values indicate the highly significant differences in the percentage methylation between these specific cytosines in TOF cases versus controls.

Example 6

Blood spots were collected on filter paper from newborns undergoing routine screening for metabolic disorders. Newborns averaged 2 days of age at the time of collection. Completely de-identified (to researchers) residual blood spots not used for metabolic testing was stored at room temperature at the Michigan Department of Community Health facilities in Lansing, Mich. DNA was extracted and purified from a single spot of blood on filter paper as described previously in the application and methylation levels in different CPG islands determined using the Illumina's Infinium Human Methylation450 Bead Chip system as described earlier.

The level or percentage methylation at multiple cytosine throughout the DNA was compared in 8 cases of hypoplastic left heart syndrome (HLHS) type CM versus 32 normal cases. Table 6 shows 4 cytosine loci located in known genes that were associated with significant differences in methylation between HLHS cases and the normal cases. The GENE ID number(s) and GENE symbols are provided along with the contribution (marginal contribution) of each particular cytosine locus for the overall prediction of HLHS versus normal non-cardiac cases. The extremely low FDR values indicate the highly significant differences in the percentage methylation between these specific cytosines in HLHS cases versus controls.

Example 7

Blood spots were collected on filter paper from newborns undergoing routine screening for metabolic disorders. Newborns averaged 2 days of age at the time of collection. Completely de-identified (to researchers) residual blood spots not used for metabolic testing was stored at room temperature at the Michigan Department of Community Health facilities in Lansing, Mich. DNA was extracted and purified from a single spot of blood on filter paper as described previously in the application and methylation levels in different CPG islands determined using the Illumina's Infinium Human Methylation450 Bead Chip system as described earlier.

The level or percentage methylation at multiple cytosine throughout the DNA was compared in 66 cases of CHD group overall (all CHD categories combined) versus 32 normal cases. Table 7 shows 8 cytosine loci located in known genes that were associated with significant differences in methylation between CHD cases and the normal cases. The GENE ID number(s) and GENE symbols are provided along with the contribution (marginal contribution) of each particular cytosine locus for the overall prediction of CHD overall versus normal non-cardiac cases. The extremely low FDR values indicate the highly significant differences in the percentage methylation between these specific cytosines in CHD cases overall versus controls.

Example 8

We also evaluated whether methylation status at cytosine loci could be used to distinguish common types of CHD from each other. In this particular analysis we distinguished 8 cases of isolated VSD from 14 TOF cases. Blood spots were collected on filter paper from newborns undergoing routine screening for metabolic disorders. Newborns averaged 2 days of age at the time of collection. Completely de-identified residual blood spots not used for metabolic testing was stored at room temperature at the Michigan Department of Community Health facilities in Lansing, Mich. DNA was extracted and purified from a single spot of blood on filter paper as described previously in the application and methylation levels in different CPG islands determined using the Illumina's Infinium Human Methylation450 Bead Chip system as described earlier.

The level or percentage methylation at multiple cytosine throughout the DNA was compared in 8 cases of isolated VSD versus 14 cases tetralogy of Fallot (TOF) type CHD. Table 8 shows 2 cytosine loci located in known genes that were associated with significant differences in methylation between VSD cases and the normal cases. The extremely low FDR values indicate the highly significant differences in the percentage methylation between these specific cytosines in isolated VSD versus TOF cases.

Example 9

Diagnostic Accuracy of Methylation Markers and Demographic Characteristics for CHD Detection.

Only limited demographic information was available from patient birth certificates and provided by the Michigan Department of Community Health (MDCH). Based on the terms of the Internal Review Board (IRB), all information was completely anonymized and chart review was precluded. The demographic features were newborn gender, birth weight, gestational age at delivery, maternal age, interval between birth and sample collection (in hours), and time in years between specimen collection and molecular analysis. While these factors with the possible exception of race are not known to affect the development of CHD, they each could potentially affect DNA methylation level and were therefore considered with cytosine methylation status in predicting or detecting CHD. The optimal combination of cytosine methylation markers when combined with demographic characteristics for CHD prediction was investigated. Only in the case of TOF did demographic characteristics contribute meaningfully to the diagnostic value when combined with methylation markers as shown in Table 9.

All cases and controls were of white ethnicity to minimize potential variability in DNA methylation related to race. With the exception of TOF, none of these factors were found to significantly affect the risk of a child developing CHD.

Also, it appeared unlikely that length of storage of blood spot accounted for significant differences in cytosine methylation levels between CHD cases and controls.

For Tables 1-9, The GENE ID number(s) and GENE symbols are provided along with the contribution (marginal contribution) of each particular cytosine locus for the overall prediction of each particular CHD category.

Diagnostic Sensitivity and Specificity of DNA Methylation Markers for CHD Detection The diagnostic sensitivities and specificities of methylation markers for the detection of the different categories of CHD are shown in Tables 10-18. Overall, high sensitivities and specificities were achieved using limited numbers of methylation markers.

Example 10

Diagnostic Accuracy of Methylation Markers for Detection of Overall CHD Group Based on Logistic Regression Analysis.

As previously noted, logistic regression analysis can be used to estimate individual risk of CHD and based on this sensitivity and specificity values calculated. Because of the small number of CHD cases in individual categories of CHD, there was insufficient study power to calculate sensitivity and specificity values for each category of CHD. As a result, this particular analysis was limited to the overall (combined) CHD group versus normal.

Table 19a, shows a combination of two cytosine loci for the prediction of CHD overall from normal controls. The sensitivity and specificity for the prediction of CHD overall is shown. In addition, the areas under the ROC curves and p-values confirming that the areas were statistically significant for discriminating the CHD overall from normal cases is provided. Addition of demographic information did not affect or improve CND prediction. Specific details regarding the cytosine loci of interest are provided in Table 19b.

DNA methylation testing was highly accurate in distinguishing individual CHD from normal cases.

Example 11

Alterations in DNA Methylation Identify Genes Involved in the Development of Congenital Aortic Valve Stenosis (AVS)

We undertook a study to examine genome-wide DNA methylation patterns in newborns with AVS to identify genomic regions containing disease-related genes and epigenetic changes that may contribute to CHD pathophysiology. An important objective of the study was to identify DNA methylation biomarkers, serum molecules that could potentially be used in the future for risk estimation and detection of AVS.

Genomic DNA was obtained from neonatal dried blood spots using commercial DNA extraction kits (Qiagen QIAamp®) according to manufacturer's protocol. Blood spot specimens were collected previously for the mandated newborn screening and treatment program run by Michigan Department of Community Health in the State of Michigan (MDCH). All specimens were collected between 24 and 79 hours after birth. This study was approved by both the institutional review boards from William Beaumont Hospital and the MDCH. Parents/legal guardians were notified at the time of blood collection that residual blood spots after clinical testing may be utilized for research pending review of such study requests by the MDCH. Limited demographic information was available for each subject including date of sample collection, maternal age and race, gestational age at delivery and newborn sex along with the type of CHD anomaly. Suspected or diagnosis-unknown AVS cases were excluded. Unaffected normal controls had no reported medical disorder and were matched for birth weight, gestational age at delivery, ethnicity, year of birth, and interval from specimen collection to testing. Our cohort included 24 AVS subjects and 24 controls. All specimens were de-identified by removal of further protected health information and researchers were masked to subject identity. Details of the case control cohort are available in Table 20.

Genome-wide methylation analysis using the HumanMethylation450: Genome-wide methylation analysis was performed for 48 individuals (24 AVS subjects and 24 controls) using the HumanMethylation450, Illumina's Infinium® HD BeadChip assay for methylation (Illumina, Inc., California, USA) which contains 485,577 methylation sites and requires only 500 ng of genomic DNA. These sites are equally distributed in the genome and represent 96% of RefSeq genes, 95% of CpG islands and an average of 17 CpG sites per covered gene region including the promoter, 5'UTR, coding, and 3'UTR regions. DNA methylation profiling using Illumina Infinium technology with peripheral blood lymphocytes has been used to identify CpG sites associated with disease states. The DNA samples were bisulfate converted using the EZ DNA Methylation-Direct Kit (Zymo Research, Orange, Calif.) according to the manufacturer's protocol. The fluorescently stained BeadChips were imaged by the Illumina iScan. Prior to detailed bioinformatic and statistical analysis, data preprocessing and quality control was performed including examination of the background signal intensity of both affected negative controls, the methylated and unmethylated signals, and ratio of the methylated and unmethylated signal intensities. The processing is done fully according to manufacturer's protocol and 99% of the CpG loci are determined unequivocally.

Statistical and Bioinformatic analysis. Genome-wide, gene-specific DNA methylation was measured using the Genome Studio methylation analysis package Illumina). Following the pre-processing described above, a DNA methylation β-value was assigned to each CpG site. Differential methylation was assessed by comparing the β-values per individual nucleotide at each CpG site between AVS subjects and controls. The p-value for methylation differences at each locus between case and normal groups was calculated as previously described. Filtering criteria for p-values was set at <0.05 and also <0.01 in order to identify the most differentiating cytosines. P-values were calculated with and without False Discovery Rate (FDR) correction for multiple testing (Benjamin-Hochberg test). Further analysis of the differentially methylated genes was conducted for potential biological significance. Receiver Operating Characteristic (ROC) curves and area under the ROC curves (ROC AUC) were calculated to determine diagnostic accuracy of specific cytosine loci differentiating AVS from control groups. Data were normalized using the Controls Normalization Method.

Gene ontology analysis and functional enrichment. The genes found to be differentially methylated (at FDR p-value<0.01) were uploaded to the web-based functional annotation tool DAVID V67 (DAVID/EASE, WebGestalt) for Gene Ontology analysis including gene ID conversion, bio-pathways analysis, and molecular functions of methylated and unmethylated regions. Literature data mining for co-occurrence of gene names and keywords of interest was performed using Chilibot. Only genes for which Entrez identifiers were available were further analyzed. Pathway analysis was carried out using Ingenuity pathway analysis (Ingenuity Systems). Over-represented canonical pathways, biological processes and molecular processes were identified.

There were no differences in gestational age at birth in weeks: mean (SD) 38.75 (1.42) in AVS subjects vs 38.88 (1.19) in controls (p=0.743), nor in the timing of specimen collection after birth (in hours), mean (SD) 31.042 (11.86) in AVS subjects vs 32.46 (8.62) in controls (p=0.638). There were no differences in maternal age 29.87 (4.56) in AVS subjects vs 29.87 (4.56) years in controls (p-value 1.00). Finally, maternal race and newborn gender were matched for analysis. In this study, we identified 3346 CpG methylation sites located in 1835 different genes by genome-wide methylation analysis of a screen cohort of AVS subjects. Of the 1835 genes identified, hierarchical clustering analysis demonstrated ~110 as novel principal candidate genes that are commonly methylated and whose methylation was associated with altered gene expression in AVS individuals. Tables 21A and 21B list the top 100 differentially methylated CpG sites based on FDR-corrected p-values. The methylation status is represented as percentage methylation for a given probe in the sample. A positive '% m Change' value indicates an average increase in methylation status in AVS subjects compared to control samples. Similarly, a negative '% m Change' value indicates a decrease in methylation status in AVS subjects compared to controls. The p-value indicates significance of the differential methylation levels. The University of California Santa Cruz (UCSC) gene name and genomic location of the C in the CG dinucleotide and the chromosome on which it is located as provided by Illumina are shown in Tables 21A and 21B. The results obtained from the DAVID Pathway and Gene Ontology overrepresentation analysis for canonical pathways and for biological processes are presented in Tables 22 and 23, respectively. Gene Set Enrichment analysis using multiple computational tools showed no significant functional enrichment due to the relatively small size of the gene list. Therefore Gene Ontology information for all genes given in the list was obtained and classified.

DAVID pathway analysis software was used to identify molecular pathways associated with genes having differentially methylated CpG sites between AVS subjects and controls. Analysis was done on genes with at least one differentially methylated CpG site based on the uncorrected p-values. Thirty-four pathways were identified; including pathways involved in cell adhesion, graft-versus-host disease, type I diabetes mellitus, MAPK signaling, and dilated cardiomyopathy. The insulin signaling pathway had a significant fraction of genes with methylation changes.

Biological processes and metabolic function determination for these genes are shown in Table 24. Genes were further grouped according to their Gene Ontology-characterized function. Four genes were identified which have cell differentiation function (ANAPC2, BMP8B, FOXK1, and SEMA4B), seven are known to have protein binding function (FASN, FOXK1, MUS81, PKHD1, PLXNA2, PPIE, and TNIK) and twelve are known to be integral membrane proteins (ANO10, ATP9B, C6orf10, FAM26F, GRAMD1B, KHDC1, MMEL1, OMA1, PKHD1, SDK1, SEMA4B, and TMC3).

In combination with the FDR p-value indicating methylation status, the area under the ROC curves can be used to distinguish AVS subjects from normal controls. A total of 57 CpG sites have ROC AUC≥0.75 with another 333 CpG sites with ROC AUC≥0.70 but <0.75. At each locus, the FDR p-value for methylation difference between AVS subjects and controls was highly significantly different.

In our study, genes involved in insulin signaling and multiple insulin receptor genes appeared from pathway over-representation analysis to play a significant role in AVS development. Studies in murine models indicate a profound change in cardiac gene expression in the hearts of fetuses of diabetic mice. The genes involved in molecular signaling pathways including apoptosis, proliferation, migration and differentiation in the developing heart were found to be differentially expressed. Among the identified 34 pathways associated with AVS in our study, insulin signaling was the most significantly over-represented pathway, with the genes NR2F2, IRS1 and IRS4 showing methylation changes. Both NR2F2 and IRS1 are located at the chromosome 15q26.2-q26.3 region. Moreover, the two genes are located within a 2.64-Mb region with the 3' end of NR2F2 and the 5' region of IGF1R separated by 2.3-Mb. These genes, therefore, represent two members of a gene cluster on chromosome 15q26.2 shown to be associated with diabetes and in this study with AVS.

The two other genes displaying altered methylation that are involved in the insulin signaling pathway are insulin receptor substrate 1 (IRS1, OMIM 147545) on chromosome 2q36.3, and insulin receptor substrate 4 (IRS4, OMIM 300904) on chromosome Xq22.3. IRS1, found in a variety of insulin-responsive cells and tissues, is involved in regulating the renin-angiotensin system in the heart which is important for the protection of myocytes from ischemic insult and is implicated in the development of insulin resistance and diabetes.

Other important differentially-methylated genes identified by Gene Ontology analysis are the collagen type VI alpha-1 (COL6A1, MIM 120220) and collagen type VI alpha-2 (COL6A2, MIM 120240) subunits. The COL6A1/COL6A2 gene cluster is mapped to chromosome 21q22.3 region and codes for a ubiquitously expressed extracellular matrix protein. There are several reports showing the involvement of COL6A1/COL6A2 genes in both syndromic and nonsyndromic congenital heart defects. The extracellular matrix is well known to play a crucial role in valvular embryogenesis. Collagen fibers are the main extracellular structures in the extracellular matrix in the heart including the valves. Several different collagen types, including type VI, have been reported to segregate in distinct compartments of the embryonic heart valves and have different functions in the valve leaflets and supporting structures. Collagen genes have been shown to be highly expressed in the immature extracellular matrix and levels of expression are reduced later in embryogenesis when the cardiac valves are remodeled. Thus abnormal transcription of collagen genes could plausibly lead to congenital valvular abnormalities.

PLXNA2 (OMIM 601054), which codes for a plexin protein, was also differentially methylated. This protein plays a role in cardiac neural crest migration during embryonic development. Neural crest cells themselves play a critical role in cardiac development. The ATP9B (OMIM 614446) gene on chromosome 18q23 region was also found to be differentially methylated in our study.

We have demonstrated profound methylation differences in multiple CpG sites in different genes in AVS. These methylation levels of individual CpG sites were used to calculate area under the ROC curves as measure of the accuracy of a putative diagnostic test with 57 CpG sites with ROC AUC≥0.75 and 333 CpG sites with ROC AUC≥0.70. This raises the possibility of using a large number of different marker combinations for effective detection of AVS.

TABLE 1

Methylation Markers and Detection of Isolated VSD from Normals: GMAX analysis

| Locus | GENE ID | GENE SYMBOL | Chromosome # | Position | Strand | FDR | Marginal Contribution (%) |
|---|---|---|---|---|---|---|---|
| cg00729708 | NM_178842 | LASS3 | 15 | 101084442 | R | 3.68E−38 | 37.14 |
| cg00095677 | NM_174954 NM_174955 NM_174956 | ATPZA3 | 17 | 3833739 | R | 4.03E−36 | 20.00 |
| cg00212031 | NM_001543 | TTTY14 | Y | 21239348 | R | 4.03E−36 | 11.43 |
| cg01014265 | NM_001083909 | GPR123 | 10 | 134940829 | R | 4.03E−36 | 11.43 |
| cg00391320 | NM_025247, NM_001136538 | ACAD10 | 12 | 112127825 | F | 4.03E−36 | 11.43 |
| cg00291929 | NM_001003811, NM_031276 | TEX11 | X | 70129657 | R | 4.03E−36 | 8.57 |

TABLE 2

Methylation Markers and Detection of ASD from Normals: GMAX Analysis

| Locus | GENE ID | GENE SYMBOL | Chromosome # | Position | Strand | FDR | Marginal Contribution (%) |
|---|---|---|---|---|---|---|---|
| cg00571519 | NM_182691, NM_182692 | SRPK2 | 7 | 104881282 | R | 1.00E−34 | 28.57 |
| cg00814218 | NM_030631, NM_001171170 | SLC25A21 | 14 | 37445440 | F | 1.00E−34 | 18.10 |
| cg01463139 | NM_001004473 | OR1OK1 | 1 | 158435277 | R | 1.00E−34 | 15.24 |
| cg01695532 | NM_003162 | STRN | 2 | 37190024 | R | 1.00E−34 | 15.24 |
| cg00762003 | NM_001037553, NM_020132 | AGPAT3 | 21 | 45393541 | F | 1.00E−34 | 11.43 |
| cg02119693 | NM_001130158, NM_001161819, NM_012223 | MYO1B | 2 | 192161142 | F | 1.00E−34 | 9.52 |
| cg00338852 | NM_182896, NM_144996 | ARL13B | 3 | 93773657 | F | 1.00E−34 | 1.90 |

TABLE 3

Methylation Markers and Detection of Pulmonary Stenosis from normal: GMAX Analysis

| Locus | GENE ID | GENE SYMBOL | Chromosome # | Position | Strand | FDR | Marginal Contribution (%) |
|---|---|---|---|---|---|---|---|
| cg00859877 | NM_00859877, NM_130842, NM_130843 | PTPRN2 | 7 | 158246263 | 7 | 1.24E−34 | 80.72 |
| cg02891314 | NM_005110 | GFPT2 | 5 | 179741120 | F | 1.24E−34 | 7.62 |
| cg01192554 | NM_003626 | PPFIA1 | 11 | 70228615 | F | 1.24E−34 | 4.26 |
| cg00159953 | NM_058175, NM_001849, NM_058714 | COL6A2 | 21 | 47547796 | R | 1.24E−34 | 4.04 |
| cg00616572 | NM_144674 | TEKT5 | 16 | 10772249 | F | 1.24E−34 | 1.79 |
| cg01029331 | NR_003264 | SDHAP1 | 3 | 195709661 | R | 1.24E−34 | 1.51 |

TABLE 4

Methylation markers and Detection of Coarctation from Normals: GMAX Analysis

| Locus | GENE ID | GENE SYMBOL | Chromosome # | Position | Strand | FDR | Marginal Contribution (%) |
|---|---|---|---|---|---|---|---|
| cg01406776 | NM_001101667, NM_003501 | ACOX3 | 4 | 8386748 | R | 5.46E−35 | 30.18 |
| cg03067774 | NM_173685 | NSMCE2 | 8 | 126341151 | F | 5.46E−35 | 19.53 |
| cg02628858 | NM_001033602 | MTUS2 | 13 | 29910801 | R | 5.46E−35 | 17.16 |
| cg01491428 | NM_001089 | ABCA3 | 16 | 2334163 | F | 5.46E−35 | 10.06 |
| cg00939438 | NM_015589, NM_001161576 | SAMD4A | 14 | 55151579 | R | 5.46E−35 | 8.88 |
| cg01178063 | NM_207320 | OTUD6A | X | 69283055 | F | 5.46E−35 | 8.28 |
| cg01426558 | NM_004660, NM_001122665 | DDX3Y | Y | 15015682 | F | 5.46E−35 | 5.92 |

TABLE 5

Methylation markers for the Detection of Tetralogy of Fallot from Normals: GMAX Analysis

| Locus | GENE ID | GENE SYMBOL | Chromosome # | Position | Strand | FDR | Marginal Contribution (%) |
|---|---|---|---|---|---|---|---|
| cg01463139 | NM_001004473 | OR1OK1 | 1 | 158435277 | R | 6.16E−35 | 29.76 |
| cg00063477 | NM_004681 | EIF1AY | Y | 22741795 | F | 6.16E−35 | 16.67 |
| cg00675157 | NM_000807, NM_001114175 | GABRA2 | 4 | 46381220 | R | 16.16E−35 | 11.90 |

TABLE 5-continued

Methylation markers for the Detection of Tetralogy of Fallot from Normals: GMAX Analysis

| Locus | GENE ID | GENE SYMBOL | Chromosome # | Position | Strand | FDR | Marginal Contribution (%) |
|---|---|---|---|---|---|---|---|
| cg00892703 | NM_014427, NM_153636 | CPNE7 | 16 | 89660342 | R | 16.16E−35 | 11.90 |
| cg01695532 | NM_003162 | STRN | 2 | 37190024 | R | 6.16E−35 | 11.90 |
| cg02363653 | NM_001163034, NM_020761 | RPTOR | 17 | 78815421 | F | 16.16E−35 | 8.33 |
| cg02907689 | NM_032512 | PDZD4 | 12 | 130195357 | F | 16.16E−35 | 7.14 |
| cg00211215 | NM_002124 | HLA-DRB1 | 6 | 32552246 | F | 16.16E−35 | 2.38 |

TABLE 6

Methylation Markers for the Detection of Hypoplastic Left Heart Syndrome from Normals: GMAX Analysis

| Locus | GENE ID | GENE SYMBOL | Chromosome # | Position | Strand | FDR | Marginal Contribution (%) |
|---|---|---|---|---|---|---|---|
| cg00256081 | NM_000512 | GALNS | 16 | 88901299 | F | 2-02E−36 | 33.00 |
| cg02091607 | NM_000294 | PHKG2 | 16 | 30760815 | F | 2-02E−36 | 25.00 |
| cg00238468 | NM_000122 | ERCC3 | 2 | 128049602 | F | 2-02E−36 | 25.00 |
| cg01510380 | NM_000744 | CHRNA4 | 20 | 61981518 | R | 2-02E−36 | 16.67 |

TABLE 7

Methylation Markers and the Detection of CHD* overall from normals: GMax analyses

| Locus | GENE ID | GENE SYMBOL | Chromosome # | Position | Strand | FDR | Marginal Contribution (%) |
|---|---|---|---|---|---|---|---|
| cg00675157 | NM_000807, NM_001114175 | GABRA2 | 4 | 46381220 | R | 1.64E−34 | 15.32 |
| cg02403522 | NM_001145399, NM_001584 | MPPED2 | 11 | 30474351 | F | 6.48E−13 | 14.37 |
| cg01463139 | NM_001004473 | OR1OK1 | 1 | 158435277 | R | 1.36E−34 | 13.31 |
| cg00999163 | NM_001136140, NM_016308 | CMPK1 | 1 | 47799638 | F | 3.21E−12 | 12.14 |
| cg00762003 | NM_001037553, NM_0210132 | AGPAT3 | 21 | 45393541 | F | 1.36E−34 | 11.43 |
| cg01406776 | NM_001101667, NM_003501 | ACOX3 | 4 | 8386748 | R | 2.65E−12 | 9.19 |
| cg01208126 | NM_001164479, NM_001164478 | FLJ44606 | 5 | 126409573 | F | 1.36E−34 | 7.30 |
| cg00443543 | NM_000934, NM_001165920, NM-001165921 | SERPINF2 | 17 | 1645410 | F | 7.13E−06 | 2.24 |

*CHD - ASD, VSD, coarctation of the aorta, pulmonary stenosis, hypoplastic left heart syndrome and tetralogy of Fallot

TABLE 8

Methylation Markers for the detection of Tetralogy of Fallot from VSD (VSD as reference group): G-Max Analysis

| Locus | Gene ID | Gene Symbol | Chromosome # | Position | Strand | FDR | Marginal Contribution (%) |
|---|---|---|---|---|---|---|---|
| cg02012379 | NM_001039567 | RPS4Y2 | Y | 22917894 | R | 2.01E−35 | 66.67 |
| cg00542384 | NM_001098728, NM_001042490 | GTF2H2C, GTF2H2D | 5 | 68868293 | F | 2.01E−35 | 33.33 |

TABLE 9

Combined methylation markers and demographic characteristics - Prediction of TOF from normal: G-max analysis

| Locus | Gene ID | Gene Symbol | Chromosome # | Position | Strand | Marginal Contribution |
|---|---|---|---|---|---|---|
| Baby age | — | — | | | | 57.48 |
| cg01655658 | NR_027822 | HLA-L | 6 | 30227583 | F | 17.38 |
| cg00095677 | NM_174954 | ATP2A3 | 17 | 3833739 | R | 8.02 |
| cg03052502 | NR_001553 | FAM197Y2 | Y | 9193029 | F | 6.68 |
| Male gender | — | — | | | | 4.01 |
| cg00045070 | NM_174936 | PCSK9 | 1 | 55504649 | R | 2.67 |

NB (8 of 9 TOF cases were males)
Baby age - number of hour between birth and blood sample collection

TABLE 10

Combined Methylation markers for Detection of VSD from Normals: GMAX Analysis

| Sensitivity (%) | Specificity (%) | AUC | P-value |
|---|---|---|---|
| 100.0 | 93.75 | 0.9844 | <0.000001 |

Combined methylation markers (see Table 1 for individual markers)

TABLE 11

Combined Methylation markers for Detection of ASD from Normals: GMAX Analysis

| Sensitivity | Specificity | AUC | P-value |
|---|---|---|---|
| 100.0 | 96.88 | 0.9952 | <0.000001 |

TABLE 12

Combined methylation markers and the Detection of Pulmonary Stenosis from Normals: GMAX Analysis

| Sensitivity (%) | Specificity (%) | AUC | P-value |
|---|---|---|---|
| 91.67 | 96.88 | 0.974 | <0.000001 |

See Table 3 for individual methylation markers.

TABLE 13

Combined methylation markers and the Detection of Coarctation from Normals: GMAX Analysis

| Sensitivity (%) | Specificity (%) | AUC | P-value |
|---|---|---|---|
| 100.0 | 93.75 | 0.974 | <0.000001 |

See Table 4 for individual methylation markers.

TABLE 14

Combined Methylation markers for the Detection of Tetralogy of Fallot from Normals: GMAX

| Sensitivity | Specificity | AUC | P-value |
|---|---|---|---|
| 70.0 | 93.75 | 0.919 | 0.00014 |

* see Table 5 for individual methylation markers

TABLE 15

Methylation markers and the Detection of Hypoplastic Left Heart Syndrome vs Normals: GMAX Analysis

| Sensitivity | Specificity | AUC | P-value |
|---|---|---|---|
| 100.0 | 93.75 | 0.9844 | 0.000001 |

*Combined methylation markers (see table 6 for individual markers)

TABLE 16

Methylation markers and the Detection of CHD overall** from control group: GMAX Analysis

| Sensitivity | Specificity | AUC | P-value |
|---|---|---|---|
| 82.81 | 78.13 | 0.8535 | <0.000001 |

*Combined methylation markers (see Table 7 for individual methylation markers)
**CHD: ASD, VSD, coarctation of the aorta, pulmonary stenosis, hypoplastic left heart syndrome and tetralogy of Fallot

TABLE 17

Methylation markers and the detection of Tetralogy of Fallot from VSD Cases: G-Max Analysis

| Sensitivity | Specificity | AUC | P-Value |
|---|---|---|---|
| 100.0 | 100.0 | 1.0 | 0.000023 |

*See table 8 for methylation loci used

TABLE 18

Methylation markers for the detection of Tetralogy of Fallot from normals: GMAX Analysis

| Sensitivity | Specification | AUC | P-Value |
|---|---|---|---|
| 88.89 | 100.00 | 0.9821 | <0.000001 |

TABLE 19a

Methylation and Demographic* Markers for the detection of CHD overall* from Normal group: Logistic Regression Analysis

| Loci (Combined) | Sensitivity | Specification | AUC (95% CI) | P-Value |
|---|---|---|---|---|
| cg00675157 + cg00999163 | 50.8 | 87.1 | 0.725 (0.65, 0-83) | <0.001 |

CHD overall: ASD, VSD, coarctation of the aorta, pulmonary stenosis, hypoplastic left heart syndrome and tetralogy of Fallot.
*Demographic markers non-significant

TABLE 19b

Cytosine Loci displaying Differential Methylation: Detection of CHD overall* from Normal group

| Loci (Combined) | Gene ID | Gene Symbol | Chromosome # | Position | Strand |
|---|---|---|---|---|---|
| Cg00675157 | NM_000807 NM_001114175 | GABRA2 | 4 | 463181220 | R |
| Cg00999163 | NM_001136140 | CMPK1 | 1 | 47799638 | F |

TABLE 20

Details of the AVS subject cohort and controls used in the present analysis.

| S. No | Sex | Mom Age (years) | Race | Gestational age at birth (weeks) | Age at Collection (hours) | status |
|---|---|---|---|---|---|---|
| 1 | male | 21 | white | 38 | 40 | Control |
| 2 | male | 28 | white | 39 | 26 | Control |
| 3 | male | 29 | white | 37 | 26 | Control |
| 4 | male | 18 | white | 40 | 24 | Control |
| 5 | female | 33 | white | 40 | 36 | Control |
| 6 | male | 30 | white | 37 | 44 | Control |
| 7 | female | 31 | black | 40 | 24 | Control |
| 8 | male | 27 | white | 40 | 24 | Control |
| 9 | male | 29 | white | 38 | 24 | Control |
| 10 | male | 33 | black | 40 | 24 | Control |
| 11 | male | 25 | white | 40 | 79 | Control |
| 12 | male | 30 | black | 38 | 25 | Control |
| 13 | male | 38 | white | 38 | 29 | Control |
| 14 | male | 36 | white | 38 | 36 | Control |
| 15 | male | 31 | white | 40 | 25 | Control |
| 16 | male | 31 | white | 39 | 29 | Control |
| 17 | male | 34 | white | 37 | 36 | Control |
| 18 | male | 28 | white | 39 | 36 | Control |
| 19 | male | 31 | white | 38 | 24 | Control |
| 20 | male | 33 | white | 39 | 25 | Control |
| 21 | female | 37 | white | 38 | 34 | Control |
| 22 | female | 27 | white | 40 | 27 | Control |
| 23 | male | 28 | black | 40 | 24 | Control |
| 24 | female | 29 | white | 41 | 24 | Control |
| 1 | male | 21 | white | 37 | 37 | Case |
| 2 | male | 28 | white | 39 | 32 | Case |
| 3 | male | 29 | white | 40 | 24 | Case |
| 4 | male | 18 | white | 38 | 36 | Case |
| 5 | female | 33 | white | 40 | 28 | Case |
| 6 | male | 30 | white | 35 | 38 | Case |
| 7 | female | 31 | black | 39 | 30 | Case |
| 8 | male | 27 | white | 40 | 34 | Case |
| 9 | male | 29 | white | 38 | 30 | Case |
| 10 | male | 33 | black | 37 | 24 | Case |
| 11 | male | 25 | white | 40 | 66 | Case |
| 12 | male | 30 | black | 39 | 36 | Case |
| 13 | male | 38 | white | 40 | 34 | Case |
| 14 | male | 36 | white | 39 | 36 | Case |
| 15 | male | 31 | white | 38 | 24 | Case |
| 16 | male | 31 | white | 38 | 36 | Case |
| 17 | male | 34 | white | 39 | 28 | Case |
| 18 | male | 28 | white | 40 | 24 | Case |
| 19 | male | 31 | white | 39 | 25 | Case |
| 20 | male | 33 | white | 39 | 26 | Case |
| 21 | male | 37 | white | 41 | 35 | Case |
| 22 | female | 27 | white | 40 | 30 | Case |
| 23 | male | 28 | black | 36 | 37 | Case |
| 24 | female | 29 | white | 39 | 29 | Case |

TABLE 21A

Chromosome and gene position for significantly methylated regions (AVS).

| TargetID | GeneSym | Chr | % m Change | FDRpvalue | AUC |
|---|---|---|---|---|---|
| cg01836455 | KHDC1 | 6 | 20.4249 | 1.58E-34 | 0.770833 |
| cg12134602 | C7orf45 | 7 | 18.26529 | 1.58E-34 | 0.737847 |
| cg06894070 | KRTAP5-7 | 11 | 11.57624 | 1.58E-34 | 0.732639 |
| cg10989317 | UBTD1 | 10 | 17.88675 | 1.58E-34 | 0.732639 |
| cg09281805 | FOXK1 | 7 | 18.29576 | 1.58E-34 | 0.725694 |
| cg06907930 | LOC100130015; GAS8 | 16 | 10.41784 | 1.58E-34 | 0.720486 |
| cg11045746 | FAM26F | 6 | 11.60995 | 1.58E-34 | 0.720486 |
| cg10167891 | C6orf147 | 6 | 15.81603 | 1.58E-34 | 0.710069 |
| cg03327352 | DMBX1; DMBX1 | 1 | 12.15573 | 1.58E-34 | 0.708333 |
| cg11787167 | NPAS3 | 14 | 10.7311 | 1.58E-34 | 0.701389 |
| cg16748433 | ARHGEF10 | 8 | 16.03455 | 1.58E-34 | 0.697917 |
| cg09690321 | PARP14 | 3 | 11.31954 | 1.58E-34 | 0.694444 |
| cg16733676 | SLC25A24 | 1 | 10.56734 | 1.58E-34 | 0.694444 |
| cg05970080 | C3orf26; FILIP1L | 3 | 12.433 | 1.58E-34 | 0.692708 |
| cg10662047 | GRAMD1B | 11 | 14.99642 | 1.58E-34 | 0.692708 |
| cg11035303 | ANO10 | 3 | 8.324309 | 1.58E-34 | 0.692708 |
| cg06621919 | PLXNA2 | 1 | 11.65171 | 1.58E-34 | 0.689236 |
| cg12551908 | STAG3L4 | 7 | 16.97976 | 1.58E-34 | 0.685764 |
| cg03900028 | ZNF117 | 7 | 21.66384 | 1.58E-34 | 0.684028 |
| cg18698799 | C6orf10 | 6 | 17.30089 | 1.58E-34 | 0.682292 |
| cg04028570 | OR2L13 | 1 | 8.712745 | 1.58E-34 | 0.678819 |
| cg14615128 | GRID2IP | 7 | 15.77792 | 1.58E-34 | 0.677083 |
| cg03392100 | C6orf26 | 6 | 10.24085 | 1.58E-34 | 0.675347 |
| cg13431688 | TGFBR1 | 9 | 11.58909 | 1.58E-34 | 0.671875 |
| cg19021236 | MICAL3 | 22 | 13.56331 | 1.58E-34 | 0.671875 |
| cg18847598 | ASAM | 11 | 13.2819 | 1.58E-34 | 0.668403 |

TABLE 21A-continued

Chromosome and gene position for significantly methylated regions (AVS).

| TargetID | GeneSym | Chr | % m Change | FDRpvalue | AUC |
|---|---|---|---|---|---|
| cg07703391 | BMP8B; PPIE | 1 | 14.81861 | 1.58E-34 | 0.664931 |
| cg13573375 | PIAS4 | 19 | 12.55099 | 1.58E-34 | 0.663194 |
| cg10117599 | PRKAR1B | 7 | 14.49434 | 1.58E-34 | 0.661458 |
| cg03040740 | FARP1 | 13 | 11.47812 | 1.58E-34 | 0.659722 |
| cg03979311 | GZMK | 5 | 11.85094 | 1.58E-34 | 0.645833 |
| cg09636756 | ATP9B | 18 | 11.69091 | 1.58E-34 | 0.642361 |
| cg13067974 | CYFIP1 | 15 | 9.829563 | 1.58E-34 | 0.637153 |
| cg17821453 | OMA1 | 1 | 13.60362 | 1.58E-34 | 0.631944 |
| cg13871921 | ANAPC2 | 9 | 9.911293 | 1.58E-34 | 0.630208 |
| cg08238319 | AHRR; LOC100310782 | 5 | 12.97881 | 1.58E-34 | 0.628472 |
| cg05730108 | FARP1 | 13 | 13.23627 | 1.58E-34 | 0.626736 |
| cg06330797 | RPS6KA2 | 6 | 9.578592 | 1.58E-34 | 0.611111 |
| cg01647917 | GZMM | 19 | 13.00265 | 1.58E-34 | 0.609375 |
| cg10736303 | PTPRN2 | 7 | 9.925252 | 1.58E-34 | 0.605903 |
| cg07918799 | ZC3H7B | 22 | 4.681402 | 1.58E-34 | 0.59375 |
| cg13782322 | SEMA4B | 15 | 9.762239 | 1.58E-34 | 0.586806 |
| cg19415746 | NRAP | 10 | 11.81949 | 1.58E-34 | 0.586806 |
| cg00567916 | NTNG2 | 9 | 12.93592 | 1.58E-34 | 0.564236 |
| cg17107246 | SLC25A24 | 1 | 9.620839 | 1.58E-34 | 0.560764 |
| cg16396396 | MTMR1 | X | 8.793682 | 1.58E-34 | 0.559028 |
| cg15198148 | FAAH | 1 | 9.473813 | 1.58E-34 | 0.553819 |
| cg02394572 | AMZ1 | 7 | 9.232473 | 1.58E-34 | 0.543403 |
| cg03407524 | FASN | 17 | 12.30205 | 1.58E-34 | 0.517361 |

TABLE 21B

Differentially methylated genes with Target ID, Gene ID, chromosome location and FDR p-value. for each gene methylated (AVS).

| TargetID | GeneSym | Chr | % m Change | FDRpvalue | AUC |
|---|---|---|---|---|---|
| cg20549346 | C6orf10 | 6 | 12.38047 | 1.58E-34 | 0.706597 |
| cg21209485 | MMEL1 | 1 | 13.05703 | 1.58E-34 | 0.685764 |
| cg21243064 | SEC16A | 9 | 11.31403 | 1.58E-34 | 0.598958 |
| cg21480464 | PEMT | 17 | 5.06717 | 1.58E-34 | 0.539931 |
| cg21566433 | PCSK6 | 15 | 11.60959 | 1.58E-34 | 0.666667 |
| cg22355889 | ELMOD1; LOC643923 | 11 | 8.745507 | 1.58E-34 | 0.628472 |
| cg22481673 | RD3 | 1 | 15.49966 | 1.58E-34 | 0.689236 |
| cg22535849 | SDK1 | 7 | 14.74525 | 1.58E-34 | 0.581597 |
| cg22671798 | ZNF573 | 19 | 10.63357 | 1.58E-34 | 0.706597 |
| cg22901347 | TNIK | 3 | 14.70642 | 1.58E-34 | 0.694444 |
| cg23187802 | ZCCHC24 | 10 | 20.18822 | 1.58E-34 | 0.741319 |
| cg23392381 | CTNNA2 | 2 | 12.10395 | 1.58E-34 | 0.638889 |
| cg23698271 | TIAL1 | 10 | 11.03699 | 1.58E-34 | 0.569444 |
| cg24407607 | DSE | 6 | 14.06801 | 1.58E-34 | 0.663194 |
| cg24668570 | KNDC1 | 10 | 9.863562 | 1.58E-34 | 0.706597 |
| cg25174111 | MUS81 | 11 | 13.87757 | 1.58E-34 | 0.652778 |
| cg26820259 | PICHD1 | 6 | 13.62307 | 1.58E-34 | 0.649306 |
| cg26840043 | SCGB1A1 | 11 | 14.28186 | 1.58E-34 | 0.572917 |
| cg27210166 | RPTOR | 17 | 5.929577 | 1.58E-34 | 0.567708 |
| cg27639199 | TMC3 | 15 | 16.17199 | 1.58E-34 | 0.694444 |
| cg03673787 | GAA | 17 | -26.47135 | 2.75E-34 | 0.784722 |
| cg06350542 | MCF2L | 13 | -11.79458 | 2.75E-34 | 0.722222 |
| cg10818676 | DUSP27 | 1 | -21.03017 | 2.75E-34 | 0.690972 |
| cg10920758 | KNDC1 | 10 | -17.21309 | 2.75E-34 | 0.699653 |
| cgl6664924 | GAA | 17 | -28.08836 | 2.75E-34 | 0.746528 |
| cg16542356 | C7orf50 | 7 | -15.83565 | 2.75E-34 | 0.649306 |
| cg19712277 | MMEL1 | 1 | -13.03072 | 2.75E-34 | 0.673611 |
| cg19949776 | LOC100132724; AP4E1 | 15 | -22.5041 | 2.75E-34 | 0.744792 |
| cg20060160 | NMNAT2 | 1 | -19.11658 | 2.75E-34 | 0.706597 |
| cg21498547 | DLGAP2 | 8 | -18.448 | 2.75E-34 | 0.645833 |
| cg25985455 | PSMA7 | 20 | -19.74279 | 2.75E-34 | 0.675347 |
| cg22972806 | LYPD6B | 2 | -15.70137 | 5.63E-34 | 0.696181 |
| cg05291429 | SLC43A2 | 17 | -13.89984 | 2.18E-33 | 0.657986 |
| cg14228103 | PTN | 7 | -16.0961 | 1.02E-32 | 0.694444 |
| cg02464073 | ITGB2 | 21 | -17.68375 | 4.14E-32 | 0.699653 |
| cg16310958 | ABHD12 | 20 | -13.82769 | 1.47E-31 | 0.659722 |
| cg13874759 | ENPP7 | 17 | -8.781952 | 2.76E-30 | 0.664931 |
| cg11189272 | OR4D1 | 17 | -13.50058 | 3.54E-30 | 0.604167 |
| cg00729708 | LASS3 | 15 | -16.05456 | 5.16E-29 | 0.699653 |
| cg18875674 | ARHGEF17 | 11 | -12.66072 | 1.09E-28 | 0.739583 |
| cg24688871 | C1orf93 | 1 | -14.61167 | 1.06E-27 | 0.765625 |
| cg25569462 | TRIML2 | 4 | -15.42906 | 1.42E-27 | 0.600694 |
| cg04388792 | ZNF490 | 19 | -16.06759 | 1.53E-27 | 0.638889 |
| cg05483487 | B4GALNT3 | 12 | -15.74404 | 1.13E-26 | 0.684028 |
| cg25165144 | B4GALNT3 | 12 | -16.09892 | 1.55E-26 | 0.65625 |
| cg05918715 | SHISA2 | 13 | -16.38652 | 1.85E-26 | 0.677083 |
| cg06316104 | HLA-G | 6 | -15.51456 | 2.49E-26 | 0.640625 |
| cg01471923 | SSTR4 | 20 | -12.05329 | 1.14E-24 | 0.571181 |
| cg13523718 | PTPRN2 | 7 | -10.61726 | 3.80E-24 | 0.600694 |
| cg08600378 | PRHOXNB | 13 | -15.03755 | 6.21E-24 | 0.723958 |

TABLE 22

Over-represented canonical pathways based on DAVID Pathway and Gene Ontology analysis (AVS).

| ID | Term | PValue | Fold Enrichment | FDR |
|---|---|---|---|---|
| hsa04940 | Type I diabetes mellitus | 3.15E-05 | 3.843537415 | 0.03844776 |
| hsa05332 | Graft-versus-host disease | 6.80E-05 | 3.843537415 | 0.082949484 |
| hsa04514 | Cell adhesion molecules (CAMs) | 1.26E-04 | 2.2711812 | 0.153493926 |
| hsa05330 | Allograft rejection | 6.88E-04 | 3.52324263 | 0.837275531 |
| hsa05416 | Viral myocarditis | 8.81E-04 | 2.59844783 | 1.070231221 |
| hsa05320 | Autoimmune thyroid disease | 0.00105726 | 2.93917567 | 1.283491273 |
| hsa05220 | Chronic myeloid leukemia | 0.001590623 | 2.459863946 | 1.925227617 |
| hsa04930 | Type II diabetes mellitus | 0.001777657 | 2.943986105 | 2.149356204 |
| hsa05212 | Pancreatic cancer | 0.002973325 | 2.402210884 | 3.571083945 |
| hsa04612 | Antigen processing and presentation | 0.004464095 | 2.222768626 | 5.317138974 |
| hsa05223 | Non-small cell lung cancer | 0.005626773 | 2.562358277 | 6.658717103 |
| hsa04722 | Neurotrophin signaling pathway | 0.009559486 | 1.859776169 | 11.06826871 |
| hsa05222 | Small cell lung cancer | 0.012130743 | 2.059037901 | 13.84700169 |
| hsa05213 | Endometrial cancer | 0.01224948 | 2.439167975 | 13.97337382 |
| hsa00600 | Sphingolipid metabolism | 0.016541277 | 2.660910518 | 18.42847551 |
| hsa05218 | Melanoma | 0.017537761 | 2.111238862 | 19.43209964 |
| hsa04960 | Aldosterone-regulated sodium reabsorption | 0.022074301 | 2.531110005 | 23.85945179 |
| hsa04672 | Intestinal immune network for IgA production | 0.022717403 | 2.353186172 | 24.46866983 |
| hsa04360 | Axon guidance | 0.027941723 | 1.69830723 | 29.25439327 |
| hsa04730 | Long-term depression | 0.033245077 | 2.005323869 | 33.82635356 |

TABLE 22-continued

Over-represented canonical pathways based on DAVID Pathway and Gene Ontology analysis (AVS).

| ID | Term | PValue | Fold Enrichment | FDR |
| --- | --- | --- | --- | --- |
| hsa05310 | Asthma | 0.034734479 | 2.783251232 | 35.0606421 |
| hsa05214 | Glioma | 0.042350873 | 2.013281503 | 41.048561 |
| hsa04270 | Vascular smooth muscle contraction | 0.057497284 | 1.647230321 | 51.47768772 |
| hsa05412 | Arrhythmogenic right ventricular cardiomyopathy | 0.060824178 | 1.820622986 | 53.52840533 |
| hsa04650 | Natural killer cell mediated cytotoxicity | 0.065049567 | 1.560533988 | 56.01822159 |
| hsa04914 | Progesterone-mediated oocyte maturation | 0.065104219 | 1.742999525 | 56.04960775 |
| hsa04530 | Tight junction | 0.068834369 | 1.548888212 | 58.14381164 |
| hsa04910 | Insulin signaling pathway | 0.072765157 | 1.537414966 | 60.25120056 |
| hsa05200 | Pathways in cancer | 0.078091754 | 1.300709308 | 62.95161525 |
| hsa05215 | Prostate cancer | 0.080182125 | 1.684246732 | 63.9645368 |
| hsa04010 | MAPK signaling pathway | 0.080481933 | 1.338760223 | 64.10770999 |
| hsa04120 | Ubiquitin mediated proteolysis | 0.081070329 | 1.514970952 | 64.38718099 |
| hsa02010 | ABC transporters | 0.081287603 | 2.096474954 | 64.48987376 |
| hsa05414 | Dilated cardiomyopathy | 0.097302462 | 1.629325643 | 71.35255143 |

TABLE 23

Over-represented Gene Ontology Molecular Function categories based on DAVID Pathway and Gene Ontology analysis (AVS).

| ID | Term | P-Value | Fold Enrichment | FDR |
| --- | --- | --- | --- | --- |
| GO:0048812 | neuron projection morphogenesis | 4.67E−05 | 2.048765713 | 0.085583107 |
| GO:0000902 | cell morphogenesis | 7.18E−05 | 1.755884917 | 0.13143928 |
| GO:0030182 | neuron differentiation | 7.27E−05 | 1.669505122 | 0.13317337 |
| GO:0048666 | neuron development | 7.66E−05 | 1.774355572 | 0.140348381 |
| GO:0000904 | cell morphogenesis involved in differentiation | 8.19E−05 | 1.933482928 | 0.14998464 |
| GO:0048870 | cell motility | 1.00E−04 | 1.805633731 | 0.183699137 |
| GO:0051674 | localization of cell | 1.00E−04 | 1.805633731 | 0.183699137 |
| GO:0031175 | neuron projection development | 1.11E−04 | 1.888922188 | 0.203196583 |
| GO:0007409 | axonogenesis | 1.74E−04 | 2.016632712 | 0.318992066 |
| GO:0032989 | cellular component morphogenesis | 1.87E−04 | 1.66367196 | 0.342117522 |
| GO:0048858 | cell projection morphogenesis | 1.90E−04 | 1.877451382 | 0.348351314 |
| GO:0006928 | cell motion | 2.29E−04 | 1.589119442 | 0.418693624 |
| GO:0016477 | cell migration | 2.79E−04 | 1.794776544 | 0.509956664 |
| GO:0048667 | cell morphogenesis involved in neuron differentiation | 3.53E−04 | 1.918681144 | 0.644237674 |
| GO:0032990 | cell part morphogenesis | 4.66E−04 | 1.796779643 | 0.850335172 |
| GO:0022604 | regulation of cell morphogenesis | 6.03E−04 | 2.160777867 | 1.099151798 |
| GO:0030030 | cell projection organization | 0.001000327 | 1.602479057 | 1.817687439 |
| GO:0010769 | regulation of cell morphogenesis involved in differentiation | 0.001792769 | 2.450752386 | 3.235406652 |
| GO:0007155 | cell adhesion | 0.002318492 | 1.381611658 | 4.165250214 |
| GO:0022610 | biological adhesion | 0.002446449 | 1.379640742 | 4.390284626 |
| GO:0031344 | regulation of cell projection organization | 0.003038233 | 2.252833479 | 5.424556888 |
| GO:0021954 | central nervous system neuron development | 0.004319393 | 3.317131648 | 7.627542949 |
| GO:0021953 | central nervous system neuron differentiation | 0.005377368 | 2.948561465 | 9.410092108 |
| GO:0010975 | regulation of neuron projection development | 0.005411048 | 2.358849172 | 9.466300485 |
| GO:0040007 | growth | 0.006199561 | 1.740134635 | 10.7728699 |
| GO:0048002 | antigen processing and presentation of peptide antigen | 0.00746377 | 3.369784531 | 12.83053058 |
| GO:0050770 | regulation of axonogenesis | 0.007545274 | 2.482999128 | 12.96163627 |
| GO:0018105 | peptidyl-serine phosphorylation | 0.009134554 | 3.253585064 | 15.48118442 |
| GO:0008285 | negative regulation of cell proliferation | 0.009344645 | 1.470196852 | 15.80904262 |
| GO:0019882 | antigen processing and presentation | 0.009509581 | 2.131490215 | 16.05860121 |
| GO:0009405 | pathogenesis | 0.009975228 | 7.862830573 | 16.78589373 |
| GO:0051130 | positive regulation of cellular component organization | 0.010186961 | 1.694201063 | 17.11148518 |
| GO:0044092 | negative regulation of molecular function | 0.010274885 | 1.483108761 | 17.24633524 |
| GO:0031399 | regulation of protein modification process | 0.010347355 | 1.519258789 | 17.35732824 |
| GO:0030238 | male sex determination | 0.010413716 | 5.361020845 | 17.45883989 |
| GO:0016311 | dephosphorylation | 0.010527003 | 1.761478278 | 17.6318633 |
| GO:0070555 | response to interleukin-1 | 0.011289259 | 4.162675009 | 18.78716851 |
| GO:0002474 | antigen processing and presentation of peptide antigen via MHC class I | 0.011289259 | 4.162675009 | 18.78716851 |
| GO:0007010 | cytoskeleton organization | 0.011400154 | 1.406653176 | 18.95396314 |
| GO:0010720 | positive regulation of cell development | 0.012416807 | 2.222104292 | 20.4680677 |
| GO:0007178 | transmembrane receptor protein serine/threonine kinase signaling pathway | 0.012703282 | 1.946623103 | 20.88986221 |
| GO:0018107 | peptidyl-threonine phosphorylation | 0.014562351 | 3.931415286 | 23.57611334 |
| GO:0007212 | dopamine receptor signaling pathway | 0.014562351 | 3.931415286 | 23.57611334 |
| GO:0018209 | peptidyl-serine modification | 0.014916316 | 2.721749044 | 24.07770038 |
| GO:0042127 | regulation of cell proliferation | 0.015324971 | 1.273838498 | 24.65291414 |
| GO:0060348 | bone development | 0.015440508 | 1.821875377 | 24.81479277 |
| GO:0031346 | positive regulation of cell projection organization | 0.0157363 | 2.509414013 | 25.22773039 |

TABLE 23-continued

Over-represented Gene Ontology Molecular Function categories based on DAVID Pathway and Gene Ontology analysis (AVS).

| ID | Term | P-Value | Fold Enrichment | FDR |
|---|---|---|---|---|
| GO:0051491 | positive regulation of filopodium assembly | 0.016365204 | 6.739569062 | 26.09858942 |
| GO:0051489 | regulation of filopodium assembly | 0.016365204 | 6.739569062 | 26.09858942 |

TABLE 24

Biological Process and Metabolic Function categories for over-represented pathways determined using DAVID Pathway and Gene Ontology analysis (AVS).

| ID | Term | PValue | Fold Enrichment | FDR |
|---|---|---|---|---|
| GO:0003779 | actin binding | 7.96E−06 | 1.898141303 | 0.012869107 |
| GO:0008092 | cytoskeletal protein binding | 1.78E−04 | 1.575246945 | 0.288109734 |
| GO:0019899 | enzyme binding | 5.09E−04 | 1.518020001 | 0.819896276 |
| GO:0051015 | actin filament binding | 0.001432089 | 2.863767477 | 2.29047365 |
| GO:0005516 | calmodulin binding | 0.001748109 | 2.001490236 | 2.789240049 |
| GO:0030695 | GTPase regulator activity | 0.001863098 | 1.531668477 | 2.970131542 |
| GO:0043167 | ion binding | 0.001901672 | 1.123213101 | 3.030741609 |
| GO:0005083 | small GTPase regulator activity | 0.002020395 | 1.661821273 | 3.217066406 |
| GO:0051020 | GTPase binding | 0.002123422 | 2.142267837 | 3.378485281 |
| GO:0005085 | guanyl-nucleotide exchange factor activity | 0.002430009 | 1.920289426 | 3.857341163 |
| GO:0060589 | nucleoside-triphosphatase regulator activity | 0.00301081 | 1.498290714 | 4.758392517 |
| GO:0043169 | cation binding | 0.003215394 | 1.117526653 | 5.073890889 |
| GO:0015399 | primary active transmembrane transporter activity | 0.003466619 | 2.009693065 | 5.459976051 |
| GO:0015405 | P-P-bond-hydrolysis-driven transmembrane transporter activity | 0.003466619 | 2.009693065 | 5.459976051 |
| GO:0017016 | Ras GTPase binding | 0.004213668 | 2.181111155 | 6.599364046 |
| GO:0005524 | ATP binding | 0.004348609 | 1.225240864 | 6.803794775 |
| GO:0031267 | small GTPase binding | 0.005132651 | 2.080757176 | 7.983311711 |
| GO:0032559 | adenyl ribonucleotide binding | 0.00546605 | 1.216670752 | 8.471695607 |
| GO:0046872 | metal ion binding | 0.00630552 | 1.108313132 | 9.721665549 |
| GO:0004012 | phospholipid-translocating ATPase activity | 0.006592431 | 4.670143885 | 10.14219212 |
| GO:0015247 | aminophospholipid transporter activity | 0.006592431 | 4.670143885 | 10.14219212 |
| GO:0015197 | peptide transporter activity | 0.007357438 | 5.837679856 | 11.25449932 |
| GO:0005089 | Rho guanyl-nucleotide exchange factor activity | 0.009445434 | 2.208851837 | 14.22503119 |
| GO:0005548 | phospholipid transporter activity | 0.009634133 | 3.220788886 | 14.48884159 |
| GO:0019900 | kinase binding | 0.010015067 | 1.695862305 | 15.01908503 |
| GO:0030554 | adenyl nucleotide binding | 0.010536434 | 1.191967605 | 15.73980846 |
| GO:0043395 | heparan sulfate proteoglycan binding | 0.010787509 | 5.306981687 | 16.08483858 |
| GO:0043560 | insulin receptor substrate binding | 0.010787509 | 5.306981687 | 16.08483858 |
| GO:0042626 | ATPase activity, coupled to transmembrane movement of substances | 0.011001503 | 1.928041053 | 16.37786385 |
| GO:0017137 | Rab GTPase binding | 0.011659796 | 3.113429257 | 17.27337797 |
| GO:0043492 | ATPase activity, coupled to movement of substances | 0.012008516 | 1.910513407 | 17.74394415 |
| GO:0016820 | hydrolase activity, acting on acid anhydrides, catalyzing transmembrane movement of substances | 0.013086789 | 1.893301575 | 19.18346598 |
| GO:0032555 | purine ribonucleotide binding | 0.01522472 | 1.163720494 | 21.96804817 |
| GO:0032553 | ribonucleotide binding | 0.01522472 | 1.163720494 | 21.96804817 |
| GO:0001883 | purine nucleoside binding | 0.01680425 | 1.174099259 | 23.96723786 |
| GO:0005088 | Ras guanyl-nucleotide exchange factor activity | 0.016903577 | 1.990118133 | 24.0913345 |
| GO:0001882 | nucleoside binding | 0.017583104 | 1.173330194 | 24.93523804 |
| GO:0008017 | microtubule binding | 0.018421667 | 2.108051059 | 25.96451542 |
| GO:0016887 | ATPase activity | 0.018652393 | 1.433202839 | 26.24538418 |
| GO:0032395 | MEC class II receptor activity | 0.019166345 | 3.686955699 | 26.86744238 |
| GO:0043394 | proteoglycan binding | 0.020362311 | 4.490522966 | 28.2959692 |
| GO:0017076 | purine nucleotide binding | 0.021248769 | 1.15049165 | 29.33810378 |
| GO:0005509 | calcium ion binding | 0.021527539 | 1.232328501 | 29.66256891 |
| GO:0016879 | ligase activity, forming carbon-nitrogen bonds | 0.023471065 | 1.516280482 | 31.88774253 |
| GO:0019901 | protein kinase binding | 0.025530937 | 1.66790853 | 34.17393199 |
| GO:0042623 | ATPase activity, coupled | 0.025830606 | 1.459419964 | 34.50046325 |
| GO:0000166 | nucleotide binding | 0.02728983 | 1.128531429 | 36.06889155 |
| GO:0008201 | heparin binding | 0.028723359 | 1.813648111 | 37.57533775 |
| GO:0031625 | ubiquitin protein ligase binding | 0.030598261 | 2.59452438 | 39.49538101 |
| GO:0004672 | protein kinase activity | 0.032997775 | 1.27157383 | 41.87189205 |
| GO:0001948 | glycoprotein binding | 0.035049989 | 2.5244021 | 43.83466919 |
| GO:0016881 | acid-amino acid ligase activity | 0.036968375 | 1.510245535 | 45.61306869 |
| GO:0003720 | telomerase activity | 0.039060062 | 8.756519784 | 47.49185352 |
| GO:0046979 | TAP2 binding | 0.039060062 | 8.756519784 | 47.49185352 |
| GO:0046978 | TAP1 binding | 0.039060062 | 8.756519784 | 47.49185352 |
| GO:0046977 | TAP binding | 0.039060062 | 8.756519784 | 47.49185352 |
| GO:0030247 | polysaccharide binding | 0.039340164 | 1.592094506 | 47.73877167 |
| GO:0001871 | pattern binding | 0.039340164 | 1.592094506 | 47.73877167 |
| GO:0046332 | SMAD binding | 0.039524232 | 2.284309509 | 47.90043945 |

TABLE 24-continued

Biological Process and Metabolic Function categories for over-represented pathways determined using DAVID Pathway and Gene Ontology analysis (AVS).

| ID | Term | PValue | Fold Enrichment | FDR |
|---|---|---|---|---|
| GO:0008270 | zinc ion binding | 0.043478853 | 1.11145787 | 51.26252703 |
| GO:0019905 | syntaxin binding | 0.04477335 | 2.636371548 | 52.31808787 |
| GO:0016564 | transcription repressor activity | 0.046450023 | 1.367051612 | 53.65342089 |
| GO:0032403 | protein complex binding | 0.047013494 | 1.489204045 | 54.09424636 |
| GO:0050431 | transforming growth factor beta binding | 0.04751837 | 4.670143885 | 54.48588641 |
| GO:0004674 | protein serine/threonine kinase activity | 0.048066593 | 1.303295968 | 54.90759975 |
| GO:0005160 | transforming growth factor beta receptor binding | 0.051597069 | 3.433929327 | 57.5367935 |
| GO:0032393 | MHC class I receptor activity | 0.051597069 | 3.433929327 | 57.5367935 |
| GO:0005539 | glycosaminoglycan binding | 0.052867833 | 1.584513104 | 58.44742556 |
| GO:0050750 | low-density lipoprotein receptor binding | 0.061292443 | 4.24558535 | 64.03663646 |
| GO:0015171 | amino acid transmembrane transporter activity | 0.062071844 | 1.978874527 | 64.51639653 |
| GO:0015297 | antiporter activity | 0.062674601 | 1.88866113 | 64.88329908 |
| GO:0019992 | diacylglycerol binding | 0.062674601 | 1.88866113 | 64.88329908 |
| GO:0008237 | metallopeptidase activity | 0.06513708 | 1.467394937 | 66.34557638 |
| GO:0046914 | transition metal ion binding | 0.06540145 | 1.089979722 | 66.4991234 |
| GO:0004437 | inositol or phosphatidylinositol phosphatase activity | 0.066171947 | 2.69431378 | 66.94288977 |
| GO:0003714 | transcription corepressor activity | 0.069691194 | 1.529874721 | 68.90058219 |
| GO:0019787 | small conjugating protein ligase activity | 0.074556767 | 1.477003337 | 71.42861529 |
| GO:0048365 | Rac GTPase binding | 0.076689466 | 3.891786571 | 72.47478656 |
| GO:0004842 | ubiquitin-protein ligase activity | 0.077332046 | 1.509060099 | 72.78288172 |
| GO:0015662 | ATPase activity, coupled to transmembrane movement of ions, phosphorylative mechanism | 0.079811513 | 1.982608253 | 73.94163727 |
| GO:0019904 | protein domain specific binding | 0.080219569 | 1.305100632 | 74.12784452 |
| GO:0015631 | tubulin binding | 0.084096314 | 1.63455036 | 75.83570952 |
| GO:0005319 | lipid transporter activity | 0.086665959 | 1.8532317 | 76.90882532 |
| GO:0000149 | SNARE binding | 0.091991823 | 2.208851837 | 78.99221524 |
| GO:0005275 | amine transmembrane transporter activity | 0.098450552 | 1.735526444 | 81.28219178 |
| GO:0003774 | motor activity | 0.098688085 | 1.479975175 | 81.36176871 |

TABLE 25

CpG sites with significant FDR p-value indicating methylation status and ROC AUC >0.75 appear to have a strong potential as diagnostic biomarkers for AVS.

| Target ID | GeneSym | Chr | % m Change | p-value | AUC |
|---|---|---|---|---|---|
| cg17525357 | MICALL2 | 7 | −4.921323 | 1.29E−07 | 0.890625 |
| cg18739821 | HS3ST3B1 | 17 | 4.364613 | 9.68E−06 | 0.826389 |
| cg19776593 | TRIM26 | 6 | 4.053861 | 8.37E−06 | 0.815972 |
| cg25309775 | ZNF283 | 19 | 6.127012 | 1.38E−05 | 0.814236 |
| cg18060909 | ANXA6; ANXA6 | 5 | 5.497217 | 5.24E−06 | 0.807292 |
| cg26940122 | ARHGEF16 | 1 | −2.347004 | 4.08E−06 | 0.805556 |
| cg10401356 | KCNK9 | 8 | −2.932733 | 1.38E−07 | 0.803819 |
| cg13715401 | GCNT1 | 9 | 4.319519 | 2.87E−06 | 0.798611 |
| cg02844593 | CACNA2D3 | 3 | −6.097019 | 1.07E−06 | 0.796875 |
| cg18059223 | NLRP2 | 19 | −5.676031 | 5.26E−09 | 0.793403 |
| cg22328396 | JAKMIP1 | 4 | −7.245114 | 4.86E−08 | 0.789931 |
| cg18182475 | RBPJ | 4 | 5.533046 | 6.01E−07 | 0.789931 |
| cg26999423 | GAS7 | 17 | 5.285408 | 8.80E−07 | 0.788194 |
| cg03673787 | GAA | 17 | −26.47135 | 7.36E−38 | 0.784722 |
| cg07955126 | LRPAP1 | 4 | −5.074149 | 1.10E−05 | 0.78125 |
| cg17754473 | CPLX1 | 4 | 4.991972 | 3.78E−07 | 0.779514 |
| cg23276602 | CCDC88A | 2 | 4.524076 | 7.46E−06 | 0.779514 |
| cg22218512 | ACVRL1 | 12 | 2.634782 | 3.66E−05 | 0.777778 |
| cg17611936 | PRKAG2 | 7 | −10.88095 | 2.38E−22 | 0.776042 |
| cg03718411 | CDH6 | 5 | 6.982511 | 2.64E−07 | 0.776042 |
| cg09726866 | FRAS1 | 4 | 3.428721 | 6.29E−05 | 0.776042 |
| cg18769357 | FBXO48 | 2 | 5.404347 | 4.29E−09 | 0.774306 |
| cg13353337 | LZTR1 | 22 | 6.512026 | 6.66E−16 | 0.772569 |
| cg01394339 | KHDC1 | 6 | 6.179863 | 5.93E−06 | 0.772569 |
| cg01836455 | KHDC1 | 6 | 20.4249 | 3.68E−38 | 0.770833 |
| cg10044101 | VNN2 | 6 | −5.974117 | 4.37E−05 | 0.770833 |
| cg16456423 | FLJ42709 | 5 | 7.54486 | 2.76E−11 | 0.769097 |
| cg06737308 | ENPP6 | 4 | −9.374768 | 5.46E−11 | 0.767361 |
| cg24637374 | IQGAP2 | 5 | 5.931985 | 2.12E−09 | 0.767361 |
| cg12893736 | GPRC5C | 17 | −4.274321 | 1.99E−05 | 0.767361 |
| cg24688871 | C1orf93 | 1 | −14.61167 | 3.20E−31 | 0.765625 |
| cg02096552 | DISP1 | 1 | 6.946665 | 1.67E−10 | 0.765625 |
| cg24194775 | NPR2 | 9 | −6.745026 | 2.57E−06 | 0.765625 |
| cg13828440 | KLRD1 | 12 | 6.478524 | 2.81E−09 | 0.763889 |
| cg20493718 | CSNK1D | 17 | −4.838026 | 2.10E−05 | 0.763889 |
| cg11646294 | PRLH | 2 | 5.585891 | 7.45E−08 | 0.762153 |
| cg20263165 | FLJ12825 | 12 | −4.360229 | 2.77E−07 | 0.762153 |
| cg09438522 | NR2C2 | 3 | 6.086844 | 4.62E−06 | 0.762153 |
| cg00994804 | RUNX1 | 21 | 3.648579 | 1.21E−06 | 0.760417 |
| cg12468774 | CCDC36 | 3 | 5.536917 | 2.89E−06 | 0.760417 |
| cg26085762 | GMCL1 | 2 | 3.965944 | 3.11E−06 | 0.760417 |
| cg13373703 | RYR2 | 1 | 4.987735 | 6.72E−05 | 0.760417 |
| cg05682970 | TMLHE | X | 7.323635 | 2.46E−12 | 0.758681 |
| cg10113820 | SLC45A4 | 8 | −2.939302 | 7.70E−06 | 0.758681 |
| cg21794665 | MIR320D1 | 13 | 4.378408 | 1.76E−06 | 0.756944 |
| cg04582010 | IFITM1 | 11 | 6.915152 | 2.34E−06 | 0.756944 |
| cg22605924 | C3orf50 | 3 | 4.532433 | 6.38E−06 | 0.755208 |
| cg03540175 | CCDC36 | 3 | 5.03055 | 1.26E−05 | 0.755208 |
| cg10610477 | BCL11A | 2 | −9.873503 | 4.08E−19 | 0.753472 |
| cg15999997 | LRRN1 | 3 | 5.393869 | 9.06E−07 | 0.753472 |
| cg27546118 | PARP11 | 12 | 4.024583 | 3.07E−06 | 0.751736 |
| cg26003056 | GPR98 | 5 | 4.14589 | 2.35E−05 | 0.751736 |
| cg26275264 | SDK1; SDK1 | 7 | −4.376698 | 2.35E−09 | 0.75 |
| cg06717068 | DOCK4 | 7 | 6.765521 | 1.76E−08 | 0.75 |
| cg08276565 | HCG18; TRIM39 | 6 | 7.209301 | 1.59E−07 | 0.75 |
| cg17332245 | E2F3 | 6 | 5.541241 | 5.14E−07 | 0.75 |
| cg15583241 | ST5 | 11 | −5.145496 | 1.64E−05 | 0.75 |

I claim:

1. A method of identifying and treating a human patient predisposed to having ventricular septal defect (VSD), wherein the method comprises:
obtaining a whole blood sample from a human patient;
extracting DNA from the obtained whole blood sample;

measuring the methylation level of LASS3 and ATPZA3 in the extracted DNA;

identifying the human patient as being predisposed to having VSD when LASS3 and ATPZA3 are differentially methylated in the extracted DNA in comparison to the methylation level of LASS3 and ATPZA3 in control blood samples obtained from human patients without VSD; and treating the human patient identified as being predisposed to having VSD by performing surgery.

2. The method of claim 1, wherein the patient is a fetus, a newborn, a pediatric patient, or an adult patient.

3. The method of claim 1, wherein the identified human patient is predisposed to having VSD at any time during any period of prenatal and postnatal life.

4. The method of claim 1, wherein the whole blood sample is a maternal whole blood sample.

5. The method of claim 4, wherein the maternal blood sample comprises cell free fetal DNA.

6. The method of claim 5, wherein the extracted DNA is cell free fetal DNA obtained from the maternal whole blood sample.

7. The method of claim 1, wherein measuring methylation comprises a bisulfite-based methylation assay or whole genome sequencing.

8. The method of claim 1, wherein measuring methylation comprises gene or whole genome sequencing techniques.

9. The method of claim 1, further comprising determining whether the human patient predisposed to having VSD is predisposed to an additional congenital heart defect by measuring the methylation level of two or more of OR1OK1, EIF1AY, KHDC1, C7orf45, GALNS, PHKG2, ACOX3, NSMCE2, SRPK2, SLC25A21, PTPRN2, and GFPT2 in the extracted DNA; and identifying the human patient as being predisposed to having an additional congenital heart defect wherein
(i) differential methylation of OR1QK1 and EIF1AY is indicative of a predisposition to tetralogy of fallot,
(ii) differential methylation of KHDC1 and C7orf45 is indicative of a predisposition to aortic valve stenosis,
(iii) differential methylation of GALNS and PHKG2 is indicative of a predisposition to hypoplastic left heart syndrome,
(iv) differential methylation of AC0X3 and NSMCE2 is indicative of a predisposition to coarctation of the aorta,
(v) differential methylation of SRPK2 and SLC25A21 is indicative of a predisposition to atrial septal defect, and
(vi) differential methylation of PTPRN2 and GFPT2 is indicative of a predisposition for pulmonary stenosis.

10. The method of claim 9, wherein the patient is a fetus, a newborn, a pediatric patient, or an adult patient.

11. The method of claim 9, wherein the identified human patient is predisposed to having the additional congenital heart defect at any time during any period of prenatal and postnatal life.

12. The method of claim 9, wherein the whole blood sample is a maternal whole blood sample.

13. The method of claim 12, wherein the maternal blood sample comprises cell free fetal DNA.

14. The method of claim 13, wherein the extracted DNA is cell free fetal DNA obtained from the maternal whole blood sample.

15. The method of claim 9, wherein measuring methylation comprises a bisulfite-based methylation assay or whole genome sequencing.

16. The method of claim 9, wherein measuring methylation comprises gene or whole genome sequencing techniques.

* * * * *